(12) United States Patent
Bright

(10) Patent No.: US 8,431,169 B2
(45) Date of Patent: Apr. 30, 2013

(54) NUTRACEUTICAL COMPOSITION AND METHODS OF USE

(75) Inventor: Dan Bright, Delacombe (AU)

(73) Assignee: Dacy Tech Pty Ltd, Delacombe (AU)

( * ) Notice: Subject to any disclaimer, the term of this patent is extended or adjusted under 35 U.S.C. 154(b) by 0 days.

(21) Appl. No.: 12/812,482

(22) PCT Filed: Dec. 12, 2008

(86) PCT No.: PCT/AU2008/001833
§ 371 (c)(1),
(2), (4) Date: Jul. 12, 2010

(87) PCT Pub. No.: WO2009/073930
PCT Pub. Date: Jun. 18, 2009

(65) Prior Publication Data
US 2010/0297254 A1 Nov. 25, 2010

(30) Foreign Application Priority Data
Dec. 12, 2007 (AU) ................................. 2007906770

(51) Int. Cl.
*A61K 36/00* (2006.01)
(52) U.S. Cl.
USPC .......................................... 424/776; 424/725
(58) Field of Classification Search .................. None
See application file for complete search history.

(56) References Cited

U.S. PATENT DOCUMENTS

| 4,473,551 A | * | 9/1984 | Schinitsky | 424/548 |
| 5,650,433 A | | 7/1997 | Watanabe et al. | |
| 2004/0228850 A1 | * | 11/2004 | McEwen | 424/94.61 |
| 2004/0248821 A1 | * | 12/2004 | Ziegler | 514/27 |

FOREIGN PATENT DOCUMENTS

| CN | 1899527 | * | 1/2007 |
| JP | 60193996 A | * | 10/1985 |
| KR | 20060016163 | | 2/2006 |
| WO | WO 9605164 A1 | * | 2/1996 |

OTHER PUBLICATIONS

"Osteoarthritis" Internet Archive Date: Oct. 13, 2011 [Retrieved from the Interent on Dec. 3, 2011]. Retrieved from the Internet on:.<http://www.mayoclinic.com/health/osteoarthritis/DS00019/METHOD=print&DSECTION=all>.*
Zhu et al. "Effects of Biota orientalis extract and its flavonoid constituents, quercetin and rutin on serum uric acid levels in oxonate-induced mice and xanthine dehydrogenase and xanthine oxidase activities in mouse liver." J. Ethanopharmacology vol. 93, Issue 1 (2004) 133-140. Abstract only.*
"Chinese Herbs" website (http://www.chinese-herbs.org/biota/)—accessed Aug. 2012.*
English translation of Jia (CN 1899572)—2006.*
International Search Report and Written Opinion for PCT Application No. PCT/AU2008/001833, dated Feb. 25, 2009, 19 pages.
Pearson, W. et al. Effects of simulated digests of Biota Orientalis ... American Journal of Veterinary Research 2008, vol. 69, pp. 1560-1568.
Choi, Y. et al. A pinusolide derivate, 15-methoxypinusolidic acid ... International Immunopharmacology. 2008, vol. 8, pp. 548-555.
Zhu, J. X. et al. Effects of Biota Orientalis extracts and its favolnoid constituents ... Journal of Ethnopharmacology, 2004, vol. 93, pp. 133-140.
Pearson, W. et al. Anti-inflammatory and Chondroprotective Effects of Nutraceuticals ... Molecular Nutritional Food Research, Mar. 2007, vol. 51, pp. 1020-1030.
Lai, L. T. Y et al. Dietary Platyclaudus orientalis Seed Oil Supresses ... Clinical Immunology annd Immunopathology, 1994, vol. 71, pp. 293-302.
Yoshida, S.H. et al. Dietary Juniperis virginiensis Seed Oil ... Journal of Lipid Mediators Cell Signalling, 1996, vol. 13, pp. 283-293.
Jie, M.S.F.L.K et al. Lipids in Chinese Medicine Characterization of all ... Journal of American Oil Chemists Society, vol. 65 ($), pp. 597-600, 2008.

* cited by examiner

*Primary Examiner* — Susan Hoffman
(74) *Attorney, Agent, or Firm* — ARC IP Law, PC; Joseph J. Mayo

(57) ABSTRACT

A method of treatment for cartilage degradation in an organism, which includes administering to an organism a composition including a therapeutic amount of an extract from the plant *Biota orientalis*. Several key components of the extract of *Biota orientalis* have been identified that have also been shown to have an effect in dramatically reducing and reversing cartilage degradation.

3 Claims, 15 Drawing Sheets

| Porcine Gene | Accession No. | Forward primer | Reverse primer |
|---|---|---|---|
| Cox1 | AF207823 | GGGAGTCCTTCTCCAATGTG | CATAAATGTGGCCGAGGTCT |
| Cox2 | AF207824 | ATGATCTACCCGCCTCACAC | AAAAGCAGCTCTGGGTCAAA |
| iNOS | X98196 | TGCGTTATGCCACCAACAATG | ACTCTCCAGGATGTTGTAG |
| Aggrecan | AF201722 | CAGGAGAAGAGATGCCAAC | CAGGTGATCCGAGGCTCC |
| β-actin | SSU07786 | TGCAGGTGACCATGGCC | CGGTAATGGAACACAACCCT |

TABLE 1

FIG 10

| INGREDIENT | % by weight |
|---|---|
| New Zealand Green Lipped Mussel | 50.90 |
| Abalone | 16.98 |
| Honey flavoring | 7.47 |
| Shark Cartilage Powder | 21.23 |
| 'Constituent 4' | 6.67 |

TABLE 2

FIG 11

| Nutrient | | |
|---|---|---|
| Crude protein | min | 12.5% |
| Crude fat | min | 2.5% |
| Crude fiber | max | 8.5% |
| Sodium (Na) | actual | 0.3% |
| Calcium (Ca) | actual | 0.65% |
| Phosphorus (P) | actual | 0.55% |
| Copper (Cu) | actual | 30 mg/kg |
| Vitamin A | min | 4,550 I.U./kg |
| Vitamin $D_3$ | min | 840 I.U./kg |
| Vitamin E | min | 70 I.U./kg |

TABLE 3

FIG 12

NUTRACEUTICAL COMPOSITION AND METHODS OF USE

CROSS-REFERENCE TO RELATED APPLICATIONS

This application is a National Stage entry of International Application No. PCT/AU2008/001833 filed 12 Dec. 2008, which claims the priority to Australian Application No. 2007906770, filed on 12 Dec. 2007, wherein the contents of both applications are hereby incorporated herein by reference in their entirety.

FIELD OF THE INVENTION

The present invention relates generally to nutraceutical compositions and methods of administering them for the treatment of inflammation or inflammation associated disorders and specifically to cartilage injury.

The present invention also relates to nutraceutical compositions extracts from a plant capable of treating inflammation or inflammation associated disorders.

DESCRIPTION OF THE PRIOR ART

In this specification, where a document, act or item of knowledge is referred to or discussed, this reference or discussion is not an admission that the document, act or item of knowledge or any combination thereof was at the priority date: part of common general knowledge, or known to be relevant to an attempt to solve any problem with which this specification is concerned.

The degradation of cartilage is a problem that plagues all vertebrates.

Cartilage is the smooth connective tissue located on the articular surface of bones and supports and protects the bone. When the cartilage becomes damaged the joint can no longer function normally and the surface of the cartilage thins out and loses its capacity to retain water and deteriorates with fissures appearing on the cartilage itself. Overtime, the elasticity of the cartilage is reduced and it becomes more susceptible to injury and damage. Progressive loss can result in bone-to-bone contact at specific points, which is extremely painful and prohibits normal functioning of the articulating joint.

NSAID's have long been used in the treatment of joint inflammation as a form of pain relief. However, there has been resistance to the continued use of many NSAID's due to the complications and adverse reactions that have been reported.

Shark cartilage provides significant improvement in joint health in an experimental model of immune-mediated arthritis (Pivnenko et al., 2005), and may improve sulfate uptake into new proteoglycan molecules.

Similarly, there is clinical evidence for the efficacy of perna mussel as a treatment for degenerative joint disease in dogs (Pollard et al., 2006; Bui and Bierer 2003). Abalone was incorporated, which has a high concentration of n-3 polyunsaturated fatty acids, which are known to reduce the formation of inflammatory eicosanoids (Mesa Garcia et al., 2006) and NO, (Pearson et al 2007).

OBJECT OF THE INVENTION

It is an object of the invention to provide a nutraceutical composition for the treatment of inflammation or inflammation associated disorders.

It is a further object of the invention to provide a nutraceutical composition for the stimulation of cartilage formation.

It is an object of the present invention to overcome, or at least substantially ameliorate, the disadvantages and shortcomings of the prior art.

Other objects and advantages of the present invention will become apparent from the following description, taking in connection with the accompanying drawings, wherein, by way of illustration and example, an embodiment of the present invention is disclosed.

SUMMARY OF THE INVENTION

In a first aspect of the invention, although this should not be seen as limiting the invention in any way, there is provided a method of treatment for cartilage degradation in an organism, the method including administering to an organism a composition including a therapeutic amount of an extract from a *Biota orientalis* plant.

In one embodiment the composition includes a therapeutic amount of an extract from the *B. orientalis* plant can further include an additional extract such as perna mussel extract, abalone extract or powder, shark cartilage powder or combinations thereof.

In a further embodiment, the extract is an extract from the seeds of the *B. orientalis* plant.

In a further embodiment, an extract from the *B. orientalis* plant can be produced from a simulated digest mimicking gastrointestinal function/processing.

A further aspect of the invention resides in the provision of a method of promoting chondrocyte growth, development and formation, the method including administering to an organism a therapeutic amount of an extract from the seeds of a *Biota orientalis* plant.

A further form of the invention resides in a synergistic composition including a therapeutic amount of an extract from a *Biota orientalis* plant for stimulating chondrocyte growth, development, and formation.

A further form of the invention resides in a method of treating a patient to stimulate cartilage growth or repair in vivo through stimulation of chondrocyte proliferation which comprises the step of increasing the activity of a prostanoid receptor involved in chondrocyte proliferation within said patient by an amount effective to stimulate chondrocyte proliferation.

A further form of the invention resides in a method including providing a composition including an extract from a *Biota orientalis* plant and administering the composition to a patient in an amount effective to increase activity of at least one prostanoid receptor involved in chondrocyte proliferation, wherein administering the composition to the patient stimulates chondrocyte proliferation and cartilage growth and/or repair.

A further form of the invention resides in a method of treating a patient to stimulate cartilage growth or repair in vivo through stimulation of chondrocyte proliferation which comprises the step of producing or increasing an agonistic effect on a prostanoid receptor involved in chondrocyte proliferation within said patient by an amount effective to stimulate chondrocyte proliferation.

A further form of the invention resides in a method of stimulating cartilage growth or repair in vivo through stimulation of chondrocyte proliferation which comprises the step of administering to said patient an extract of *Biota orientalis* in an effective amount to stimulate chondrocyte proliferation.

In preference, the method further includes administering the extract in combination with an extract such as shark cartilage, perna mussel extract, abalone extract or combinations thereof.

In yet a further form of the invention there is provided a therapeutic composition including an extract of *Biota orientalis* in an amount effective to stimulate chondrocyte proliferation.

In yet a further form of the invention there is provided a use of an extract from the plant *Biota orientalis* for the manufacture of a medicament for the therapeutic and/or prophylactic treatment of cartilage degenerative conditions.

In yet a further form of the invention there is a use of a composition including at least one of the compounds selected from the group consisting of (9Z,13S,15Z)-12,13-epoxyoctadeca-9,11,15-trienoic acid, cis, cis, cis-9,12,15-octadecatrienoic acid (ALA), cis, cis, cis-6,9,12-octadecatrienoic acid (GLA), cis, cis-9,12-octadecadienoic acid and 9-Octadecenoic acid for the manufacture of a medicament for the therapeutic and/or prophylactic treatment of cartilage degenerative conditions.

In preference, the medicament includes an additional extract such as perna mussel extract, abalone extract or powder, shark cartilage powder or combinations thereof.

A further form of the invention resides in a method of treatment for cartilage degenerative conditions in a mammal, which includes administering to the mammal a therapeutically effective amount of a polyunsaturated fatty acid.

In preference, the polyunsaturated fatty acid is selected from the group of omega-3, omega-6, omega-9 and conjugated fatty acids or mixtures thereof.

In preference, the omega-3 fatty acid is selected from the group including: cis,cis,cis-7,10,13-hexadecatrienoic acid; cis,cis,cis-9,12,15-octadecatrienoic acid; cis,cis,cis-6,9,12,15,-octadecatetrae-noic acid; cis,cis,cis-11,14,17-eicosatrienoic acid; cis,cis,cis,cis-8,11,14,17-eicosatetraenoic acid; cis,cis,cis,cis, cis-5,8,11,14,17-eicosapentaenoic acid; cis, cis,cis,cis,cis-7,10,13,16,19-docosapentaenoic acid; cis,cis, cis,cis,cis-4,7,10,13,16,19-docosahexaenoic acid; cis,cis, cis,cis-9,12,15,18,21-tetracosapentaenoic acid; and cis,cis, cis,cis,cis-6,9,12,15,18,21-tetracosahexaenoic acid or mixtures thereof.

In preference, the omega-6 fatty acid is selected from the group including: cis,cis-9,12-octadecadienoic acid; cis,cis, cis-6,9,12-octadecatrienoic acid; cis,cis-11,14-eicosadienoic acid; cis,cis,cis-8,11,14-eicosatrienoic acid; cis,cis,cis-5, 8,11,14-eicosatetraenoic acid; cis,cis-13,16-docosadienoic acid; cis,cis,cis,cis-7,10,13,16-docosatetraenoic acid; and cis,cis,cis,cis-4,7,10,13,16-docosa-pentaenoic acid or mixtures thereof.

In preference, the omega-9 fatty acid is selected from the group including: cis-9-octadecenoic acid; cis-11-eicosenoic acid; cis,cis,cis-5,8,11-eicosatrienoic acid; cis-13-docosenoic acid; and cis-15-tetracosenoic acid or mixtures thereof.

In preference, the conjugated fatty acid is selected from the group including: 9Z,11E-octadeca-9,11-dienoic acid; 10E, 12Z-octadeca-9,11-dienoic acid; 8E,10E,12Z-octadecatrienoic acid; 8E,10E,12E-octadecatrienoic acid; 8E,10Z,12E-octadecatrienoic acid; 9E,11E,13Z-octadeca-9,11,13-trienoic acid; 9E,11E,13E-octadeca-9,11,13-trienoic acid; 9Z,11Z,13E-octadeca-9,11,13-trienoic acid; 9Z,11E,13Z-octadeca-9,11,13-trienoic acid; 9E,11Z,15E-octadeca-9,11,13,15-trienoic acid; 9E,11Z,13Z,15E-octadeca-9,11,13,15-trienoic acid; trans,trans,trans,trans-octadeca-9,11,13,15-trienoic acid; (9E,13S,15Z)-12,13-epoxyoctadeca-9,11,15-trienoic acid; and 5Z,8Z,10E,12E,14Z-eicosanoic acid or mixtures thereof.

In preference, the above is a pharmaceutical preparation

BRIEF DESCRIPTION OF THE DRAWINGS

By way of example, an employment of the invention is described more fully hereinafter with reference to the accompanying drawings, in which:

FIG. 10: Table 1 showing the primers for aggrecan and β-actin.

FIG. 11: Table 2 showing the composition of Sasha's EQ powder prepared by combining Abalone (AB), New Zealand Green Lipped Mussel (NZGLM), Shark cartilage (SC) and BO (Interpath Pty Ltd, Australia).

FIG. 12: Table 3 showing the composition of Sasha's EQ for feeding to horses.

DETAILED DESCRIPTION OF THE INVENTION

Figure 1:
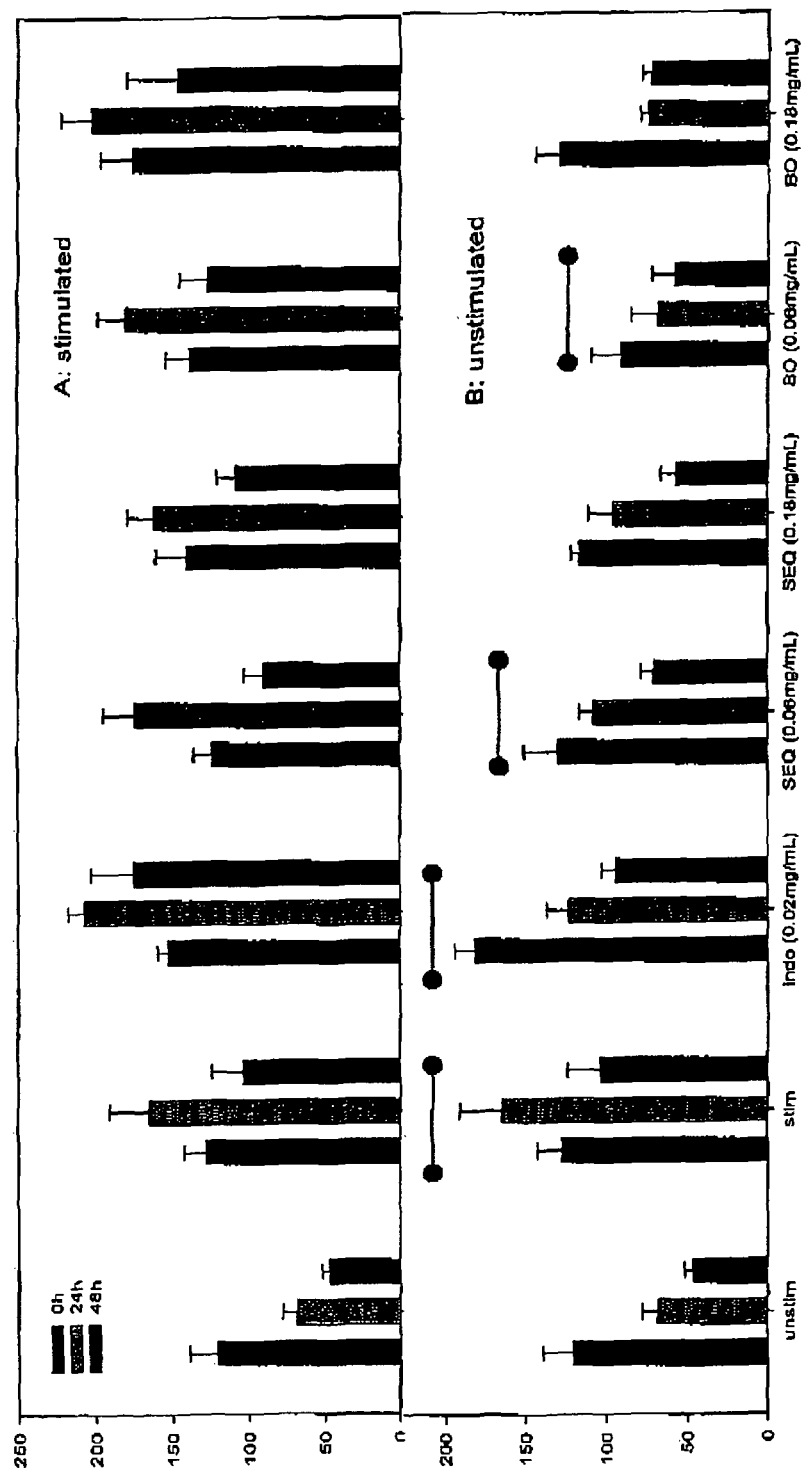
FIG. 1: GAG release by IL-1 stimulated (FIG. 1A) and unstimulated (FIG. 1B) cartilage explants. ←→ represents treatments significantly different from stimulated (A) or unstimulated (B) controls. IL-1 resulted in a significant increase in GAG release in control explants. There was no significant effect of any treatment on IL-1-stimulated explants. Indo$_{sim}$, and SEQ$_{sim}$ (0.06 mg/mL) resulted in significantly higher media [GAG] in unstimulated explants compared, with unstimulated controls. BO (0.06 mg/mL) reduced media [GAG] in unstimulated explants.
Figure 2:
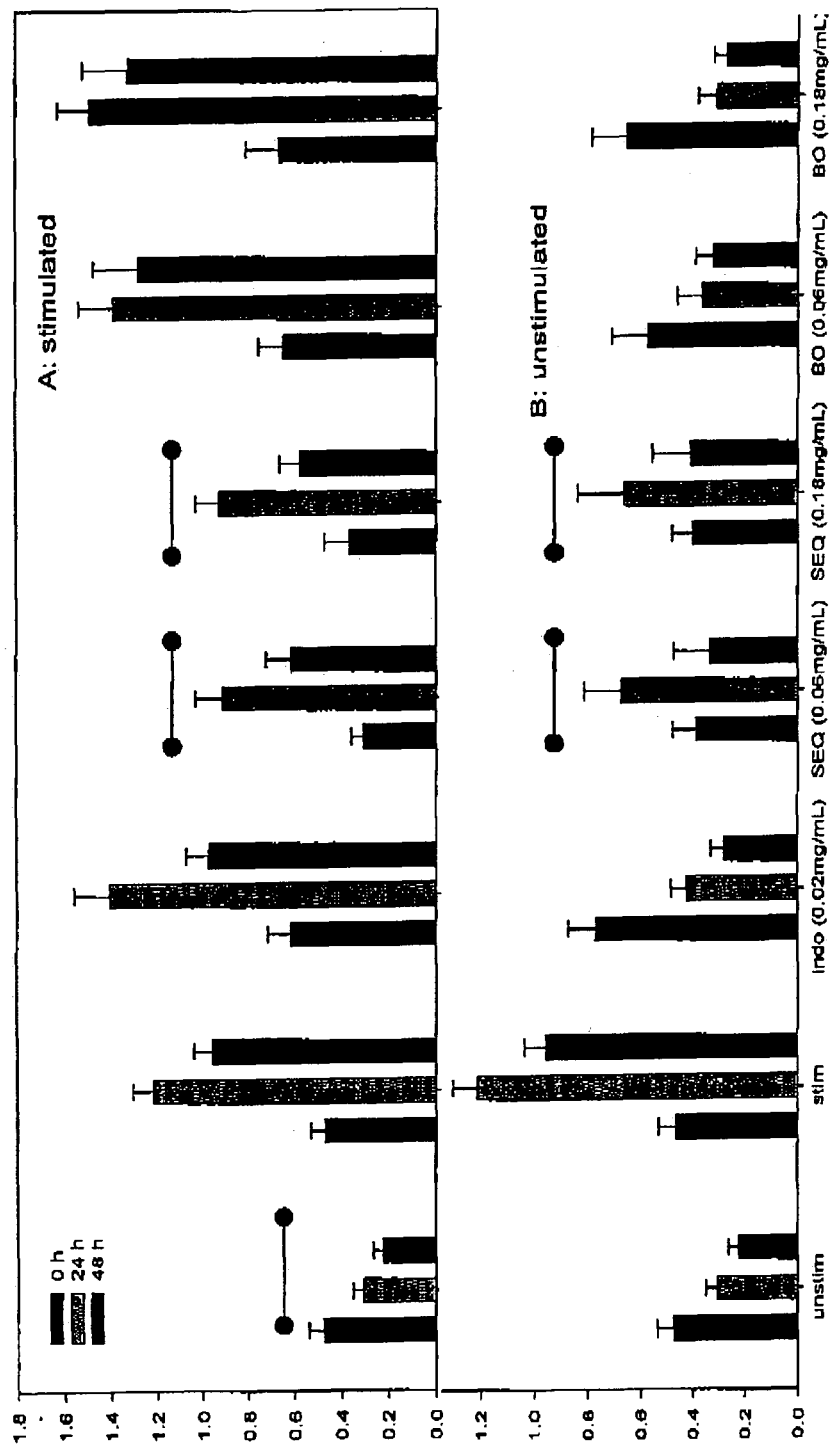
FIG. 2: Nitric oxide (NO) (measured as nitrite) in media from IL-1 stimulated (A) and unstimulated (B) cartilage explants. ←→ represents treatments significantly different from stimulated (A) or unstimulated (B) controls. IL-1 resulted in a significant increase in NO release by control explants. SEQ$_{sim}$ (both doses) resulted in a significantly higher media [NO] in unstimulated explants compared with unstimulated controls, and a significantly lower media [NO] in stimulated explants compared with stimulated controls. BO$_{sim}$ had no effect on media [NO].

To facilitate an understanding of the invention various terms and abbreviations are used and defined below:

"SEQ" means a mixture of New Zealand Green Lipped or perna mussel, abalone, shark cartilage powder and biota oil.

"BO" means biota oil extracted from the seeds of the plant *Biota orientalis*.

"NZGLM" means New Zealand Green Lipped Mussel or perna mussel.

"sim" means the simulated digest.

"COX" or "cox" means the enzyme cyclooxygenase.

"iNOS" means inducible NO synthase.

*Biota orientalis* ("*Biota*") is an herb native to Western China and North Korea and is known by a number of other names, such as *Thuja orientalis*, *Platycladus stricta*, and *Platycladus orientalis*, *Biota* is greatly valued in traditional Chinese medicine as one of the 50 fundamental herbs (Duke and Ayensu 1985). Traditionally it is used as a laxative, painkiller and sedative (Duke and Ayensu 1985).

Simulated digests of shark cartilage, NZGLM and abalone have been previously reported to have anti-inflammatory effects in a cartilage explant model of arthritis by reducing $PGE_2$ (Prostoglandin $E_2$), GAG and/or nitric oxide. (Pearson et al., 2007).

Methods

Explant Cultures

Front legs of market weight pigs (5-7 months old, 200-250 lbs) were obtained from a local abattoir. Legs were chilled on crushed ice until dissection. Using aseptic technique, the intercarpal joint was opened and the cartilage surfaces exposed. A 4 mm dermal biopsy punch was used to take explants (~0.5 mm thickness; 11-15 mg/explant) of healthy cartilage from the weight-bearing region of both articulating surfaces of the intercarpal joint. Cartilage pieces were washed 3 times in Dubelco's Modified Eagle Medium (DMEM) supplemented with $NaHCO_3$. Two cartilage discs were placed into each well of 24-well tissue culture plates containing DMEM supplemented with amino acids, sodium selenite, manganese sulfate, $NaHCO_3$ and ascorbic acid (TCM—tissue culture medium). Plates were incubated at 37° C., 7% $CO_2$ in a humidified atmosphere for up to 144 h. Every 24 h media was completely aspirated into 1 mL microcentrifuge tubes and immediately replaced with control, conditioned and/or stimulated media (described below) before being returned to the incubator. The collected media was stored at −80° C. until analysis. Cartilage was harvested at the end of each experiment with one explant per well stained for cytotoxicity and the remaining cartilage immediately frozen at −80° C.

Simulated Digestion and Ultrafiltration

A simulated digestion procedure was developed to mimic the gastrointestinal processing of ingested dietary supplements. This type of approach has previously been used to improve the bio-assessment of putative nutraceuticals (Rininger et al., 2000; Pearson et al., 2007).

Simulated digests were prepared using SEQ (0.85 g), BO [2.5 mL (0.85 g)] and indomethacin (0.074 g—a positive anti-inflammatory control). Each test substance was individually suspended in 35 mL of simulated gastric fluid (37 mM NaCl, 0.03N HCl, 3.2 mg/mL pepsin), and shaken at 37° C. for 2 h (Rininger et al., 2000). After this, solution acidity was neutralized by adding an equinormal volume of 2.2 N NaOH (1.15 mL). To this was added 36.15 mL of simulated intestinal fluid (Rininger et al., 2000–30 mM $K_2HPO_4$, 160 mM $NaH_2PO_4$; 20 mg/mL pancreatin; pH adjusted to 7.4) and the resultant mixture shaken in a 37° C. incubator for a further 2 h. A "blank" was prepared using identical methodology but without including any test substance. Appropriate volumes of gastric and intestinal fluid were derived from those approximated in a human stomach (Marciani et al., 2005).

Upon completion of the 4-hour incubation, simulated digests of SEQ ($SEQ_{sim}$) BO ($BO_{sim}$) and indomethacin ($indo_{sim}$) were centrifuged at 3,000×g for 25 min at 4° C. The supernatant was decanted and centrifuged a second time at 3,000×g for 15 min at 4° C. The resulting supernatant was warmed to room temperature and filtered (0.22 µm) to remove particulates. This filtrate was further fractioned with an ultrafiltration centrifuge unit with a 50 kDa molecular weight cut-off, (AmiconUltra, Millipore, Mississauga ON), spinning at 3,000×g for 25 min (room temperature). Filtered simulated digest was stored at 4° C. until use for a maximum of 7 days.

Effect of $SEQ_{sim}$ and $BO_{sim}$ on IL-1-Induced Inflammation $SEQ_{sim}$ was prepared as explained above. Explants from 12 pigs were prepared as previously described, and maintained in unconditioned media for the initial 24 h. At 24 hours post-culture, $SEQ_{sim}$, $BO_{sim}$, (0, 0.06 or 0.18 mg/mL) or $indo_{sim}$ (0.02 mg/mL) was added to TCM. Conditioned media was refreshed every 24 hours for the duration of the experiment. At 72 hours post-culture, and every 24 hours thereafter, explants were stimulated with IL-1 (0 or 10 ng/mL; Medicorp, Montreal, Quebec; Cat. #PHC0813). Explants from each animal were exposed to each treatment in duplicate. Explants were cultured for a total of 120 h. Media was analyzed for [$PGE_2$], [GAG], and [NO]. One explant per treatment was collected into sterile phosphate buffered saline (PBS) and immediately stained for cell viability (see below). The second explant was frozen at −80° C. for RNA extraction (see below).

GAG Analysis

Media GAG concentration was determined using a 1,9-DMB spectrophotometric assay (Chandrasekhar et al., 1987). Samples were added to 96 well plates at 50% dilution, and serially diluted 1:2 up to a final dilution of 1:64. Guanidine hydrochloride was added to all wells immediately prior to DMB dye. Plates were incubated in the dark for 10 minutes, and absorbance was read on a Victor 3 microplate reader at 530 nm. Sample absorbance was compared to that of a chondroitin sulfate standard. Standard curves were developed for each plate, and a best-fit linear equation with $R^2 \geq 0.99$ was used to calculate GAG concentrations for standards and samples.

Isolation of Total RNA and Synthesis of cDNA

Total RNA was extracted from cartilage explants using a modified TRIzol procedure (Chan et al., 2005). Frozen cartilage from each animal was pooled according to conditioning and stimulation, and homogenized in Tri-Reagent (100 mg tissue/mL; Sigma, Mississauga ON). Chloroform was added to extract RNA followed by vigorous agitation and 2-min incubation at room temperature. Sample was then centrifuged (12,000×g, 15 min) and RNA was precipitated with an equal volume of 70% ethanol (DEPC). RNA precipitate was applied to an RNeasy mini column (Qiagen, Valencia Calif., USA) and RNA was purified according to manufacturer instructions.

For each pooled sample, 1 µg total RNA was converted to single stranded cDNA using Moloney Murine Leukemia Virus (MMLV) reverse transcriptase (Invitrogen, Burlington ON) according to manufacturer instructions. Single-strand cDNA was quantified by UV spectrophotometry and diluted with DEPC-$H_2O$ to a final concentration of 10 ng/µL.

Quantitative Real Time RT-PCR

Primers for aggrecan (the primary large aggregating proteoglycan in hyaline cartilage) (Fehrenbacher et al., 2003) and β-actin (housekeeping gene; Nishimoto et al., 2005) (Table 1) were prepared (Laboratory Services Division, University of Guelph) and stored at −20° C. until use. Cartilage samples from $SEQ_{sim}$ and $BO_{sim}$ were evaluated for changes in gene expression, together with cartilage cultured under identical conditions previously with the other 3 components of SEQ (see Pearson et al., 2007 for detailed culture conditions). Twenty five microliter PCR reactions were performed in triplicate using an ABI Prism 7000 sequence detection system (Perkin-Elmer). Amplification of 50 ng of each cDNA sample was detected using SYBR-Rox (Invitrogen, Burlington ON) and compared to a standard curve of pooled cDNA containing equal amounts of cDNA from each sample. A 1.5% agarose electrophoresis gel was used to confirm PCR products. Expression of each gene of interest (G) in each sample was normalized to β-actin (β), and compared to unstimulated control explants (ie. fold change for calibrator=1).

Fold change (fc) in expression ($\Delta G/\Delta \beta$), relative to unstimulated or stimulated control as indicated, is presented in arbitrary units.

Cytotoxicity Staining

Cell viability was determined using a commercially available viability staining kit (Invitrogen; Burlington ON) (Pearson et al., 2007). Briefly, explants were washed in 500 µL PBS and placed into a 96-well microtitre plate (one explant per well), and were incubated in 200 µL of stock stain (4 µM C-AM; 8 µM EthD-1) for one hour at room temperature. The plate was read from the bottom of each well using 10 horizontal steps, 3 vertical steps, and a 0.1 mm displacement. C-AM and EthD-1 fluorescence in live and killed explants were obtained with excitation/emission filters of 485/530 nm and 530/685 nm, respectively.

Data Analysis

Data from analysis of tissue culture media and viability are presented as means±standard error. Means of replicates from each treatment/animal were analyzed using two-way repeated measures analysis of variance comparing each treatment with unconditioned controls and indomethacin-conditioned controls. Viability data were analyzed using the Student's t-test, individually comparing stimulated controls with all other treatments. When a significant F-ratio was obtained, the Holm-Sidak post-hoc test was used to identify significant differences with respect to treatment and/or time. Significance was accepted if $p \leq 0.05$.

Due to low cellularity of cartilage explants, it was necessary to pool RNA from explants exposed to the same conditioning and stimulation in order to extract sufficient RNA for a reverse transcription reaction. Thus, PCR data are presented in the text as a mean change in gene expression (calibrated to controls) relative to β-actin. A calibrated fold-expression change ≧2 is considered to be biologically relevant (Yang et al., 2002; Schena et al., 1995) and such expression changes are discussed in the text as significant differences.

Results

Gene Expression

Cox 1: All constituents of SEQ reduced cox 1 expression in unstimulated explants (range: 76-95% inhibition). Importantly, it was observed that $BO_{sim}$ (0.06 mg/mL) was the most effective cox 1 inhibitor, reducing cox 1 expression by 95% in both unstimulated and stimulated explants.

Figure 4:
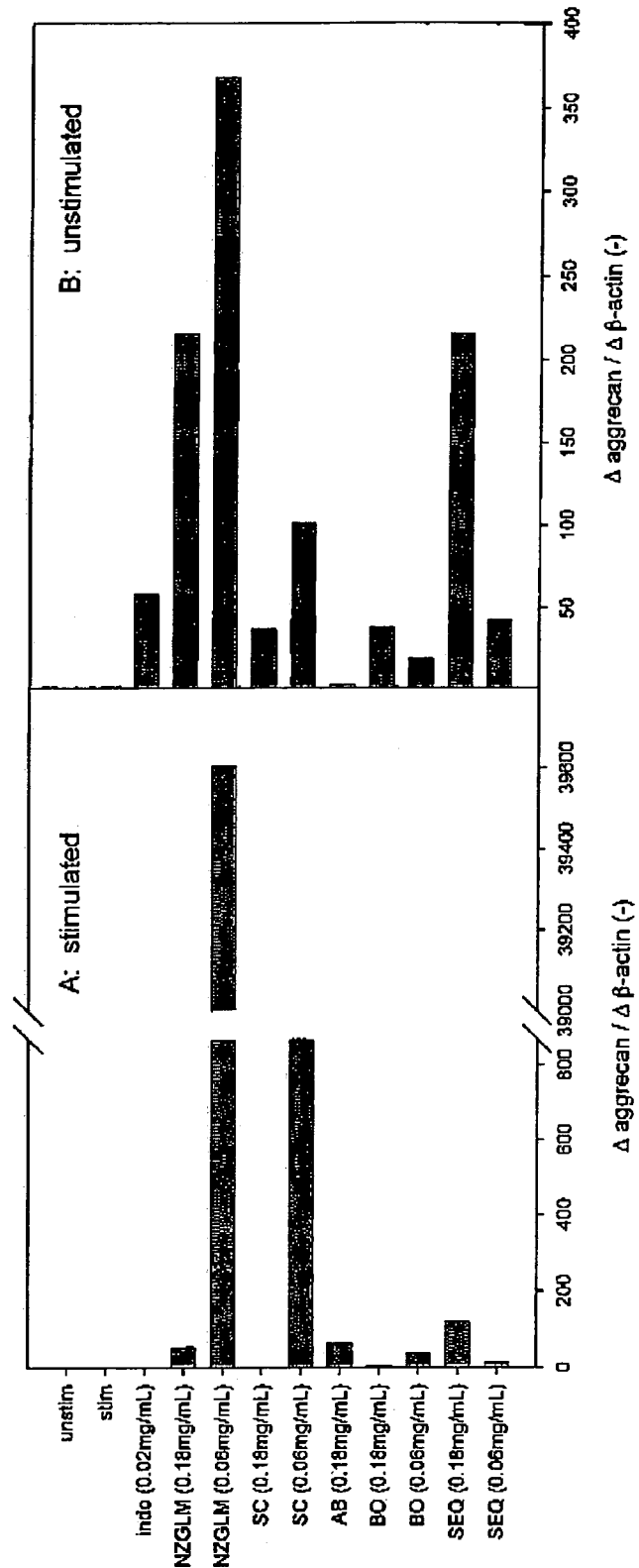
FIG. 4: Relative expression of aggrecan RNA in IL-1 stimulated (A) and unstimulated (B) cartilage explants. Stimulated (stim) and unstimulated (unstim) controls are shown on each graph for comparison. For each of A and B, treatments are compared to the stimulated (A) and unstimulated (B) controls. Unstimulated and stimulated control explants had no measurable expression of aggrecan. All treatments resulted in significant increase in aggrecan expression in unstimulated explants, the least effective of which was AB$_{sim}$. NZGLM$_{sim}$ (0.06 mg/mL) resulted in a substantial increase in aggrecan expression in both unstimulated and stimulated explants. SEQ$_{sim}$ (0.18 mg/mL) was effective in increasing aggrecan expression in both stimulated and unstimulated explants.

Aggrecan (FIG. 4, A and B): Stimulation of control explants with IL-1 resulted in a slight, non-significant decline in aggrecan expression. Conditioning of unstimulated explants with $indo_{sim}$ resulted in 58-fold increase in aggrecan. This increase was completely abolished by stimulation of $indo_{sim}$-conditioned explants with IL-1.

SEQ and all of its constituents significantly increased aggrecan expression in unstimulated explants. $SEQ_{sim}$ increased aggrecan expression in unstimulated explants in a dose-dependent manner (42.8- and 215.7-fold increase for 0.06 and 0.18 mg/mL, respectively).

Stimulation of conditioned explants with IL-1 resulted in a significant increase in aggrecan expression in SEQ and all of its constituents, with the exception of $SC_{sim}$ (0.18 mg/mL; 1.4-fold increase).

Cell Metabolism

GAG: Media [GAG] significantly declined at 24 and 48 h in unstimulated control explants. Conditioning of unstimulated explants with $indo_{sim}$ resulted in a significantly higher media [GAG] at all time points compared with unstimulated controls (FIG. 1). IL-1 stimulation (10 ng/mL) resulted in a significant elevation of media [GAG] in control explants at 24 h post-stimulation. Media [GAG] from $indo_{sim}$-conditioned explants was elevated compared with stimulated controls over the duration of the experiment, but not significantly (p=0.1). There was no significant effect of IL-1 on $indo_{sim}$-conditioned explants.

There was no significant effect of $SEQ_{sim}$ (0.06 and 0.18 mg/mL) on IL-1-induced GAG release (FIG. 1, A). Media [GAG] was significantly higher in unstimulated explants conditioned $SEQ_{sim}$ (06 mg/mL) compared with unstimulated controls (FIG. 1, B). Conditioning with $SEQ_{sim}$ (0.18 mg/mL) resulted in a non-significant increase in media [GAG] (p=0.06).

There was no effect of $BO_{sim}$ on GAG release in IL-1-stimulated explants (FIG. 1, A). Conditioning of unstimulated explants with $BO_{sim}$ (0.06 mg/mL) significantly reduced media [GAG] compared with unstimulated controls (FIG. 1, B). There was a trend to a decrease in media [GAG] from explants conditioned with $BO_{sim}$ (0.18 mg/mL) (p=0.06).

Viability: There was no significant effect of IL-1 stimulation (10 ng/mL) on cell viability. Conditioning of explants with $indo_{sim}$ had no significant effect on cell viability in unstimulated or IL-1-stimulated explants (FIG. 3).

$SEQ_{sim}$ (0.18 mg/mL) resulted in a significant increase in cell viability in IL-1-stimulated explants compared with stimulated controls (FIG. 3, A), while stimulated explants conditioned with $SEQ_{sim}$, (0.06 mg/mL) tended to increase in % viability (p=0.06). $SEQ_{sim}$ conditioning had no effect on unstimulated explants (FIG. 3, B).

Figure 3:
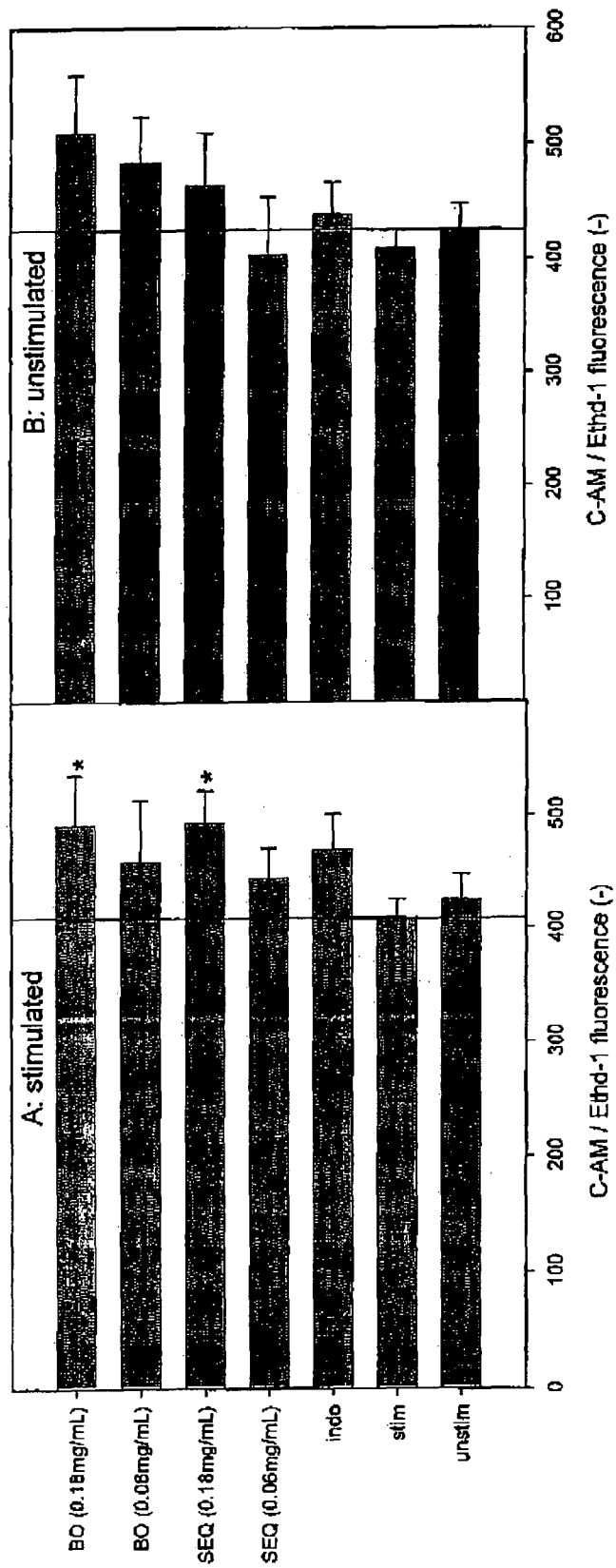
FIG. 3: Ratio of calcein-AM (C-AM) and ethidium homodimer 1 (Ethd-1) fluorescence in IL-1-stimulated and unstimulated cartilage explants. Stimulated (stim) and unstimulated (unstim) controls are included on each graph for comparison. * denotes significantly different from stimulated (A) or unstimulated (B) controls. IL-1 stimulation caused a small, non-significant decline in cell viability. There was no effect of any treatments on cell viability in unstimulated explants. SEQ$_{sim}$ and BO$_{sim}$ (0.18 mg/mL) significantly increased cell viability in IL-1-stimulated explants relative to stimulated controls.

There was a tendency for increased cell viability in unstimulated explants conditioned with $BO_{sim}$ (0.18 mg/mL) (p=0.09) (FIG. 3, B). The increase in cell viability was significant when this dose was applied to IL-1-stimulated explants (FIG. 3, A).

Discussion

The methodology described evaluated the effect of a simulated digest of SEQ and BO on cartilage metabolism, in the presence and absence of IL-1, with respect to $PGE_2$, NO, GAG and cell viability. The gene expression data was used to make predictions about a mechanism of action of SEQ.

It has also been shown that $indo_{sim}$ does not influence IL-1-mediated aggrecan expression in IL-1-stimulated explants, an effect that has been reported in mechanically stressed cartilage explants (limoto et al., 2005).

These data characterize indomethacin as an effective anti-inflammatory predominately through cox inhibition. Its inability to reduce IL-1-mediated aggrecan expression and its augmenting effect on IL-1-mediated iNOS expression, however, suggest that cartilage exposed to indomethacin would continue to degenerate through decline in matrix formation and would suffer from increased nitric oxide-mediated cell death.

Indeed these adverse effects have been reported in arthritic dogs using prophylactic indomethacin (Hungin and Kean 2001), and indomethacin is associated with worsening of some pathophyslological indicators of arthritis in humans (Rashad et al., 1989; Huakinsson et al., 1995). When $indo_{sim}$ was applied to cartilage explants in the current study, there was an increase in IL-1-mediated NO production, but this was not coupled with a decrease in cell viability. Cell death subsequent to cartilage injury has been reported 7 days after mechanical injury, and this apoptosis was mediated, to some degree, by specific blockers of iNOS activity (Green et al., 2006), whereas isolated chondrocyte-like cells underwent apoptotic changes within 48 h of exposure to 1 ng/mL IL-1 (Yasuhara et al., 2005).

However, transcriptional upregulation of aggrecan of more than 120-fold provides good evidence that SEQ is capable of stimulating formation of new cartilage in the face of inflammatory challenge by IL-1. The increase in GAGs observed in unstimulated explants conditioned with SEQ (0.06 mg/mL) was likely a reflection of an increased provision of exogenous GAGs. It is likely that this increase was not significant in explants conditioned with the higher dose because of a significantly increased formation of new proteoglycan, as demonstrated by an increase in expression of aggrecan by explants.

Furthermore, this increase in GAGs was not seen in IL-1-stimulated explants suggesting that SEQ may in fact be inhibiting IL-1-induced GAG release in addition to stimulating proteoglycan synthesis.

A final end-point which was significantly affected by SEQ and BO in the current experiment was an increase in cell viability subsequent to IL-1 challenge. This increase was not reduced apoptosis, as may be predicted from the iNOS and NO inhibitory properties of SEQ, as it did not reflect recovery of IL-1-stimulated cells back to an unstimulated state. Rather, cell viability increased above unstimulated control levels. The primary mechanism for chondrocyte growth in cartilage has been attributed to $PGE_2$ binding to one of its four cell-surface receptors, EP1, EP2, EP3 and EP4. This property has been associated specifically to EP1 (Del Toro et al., 2000; Brochhausen et al., 2006), or EP2 (Aoyama it al, 2005).

What we have now seen has been observed in the studies described herein is that $SEQ_{sim}$ and/or $BO_{sim}$, produce an increase in chondrocyte proliferation, resulting in an increase in live cell staining. This also provides a basis for the concurrent inhibition of $PGE_2$. Substances that behave as agonists for PGE$_2$ receptors act to "fool" cells into treating the agonist as if it were the target molecule (ie. PGE$_2$). So inclusion of a PGE$_2$ agonist can have a similar effect as increasing the amount of PGE$_2$ in the pericellular environment.

It is known that PGE$_2$-production from IL-1 stimulated cells is inhibited by increasing extracellular concentrations of PGE$_2$ (Akarasereenont at al., 1999).

CONCLUSIONS

The simulated digest of SEQ significantly inhibited in vitro formation of PGE$_2$ and NO in IL-1-stimulated cartilage explants, while showing no effect on GAG release and increasing cell viability. A simulated digest of *Biota orientalis*, a previously uninvestigated constituent of SEQ, inhibited release of GAGs by unstimulated cartilage explants. This constituent also significantly increased cell viability in IL-1-stimulated cartilage explants. Taken together, these data provide evidence that SEQ protects cartilage from the damaging effects of IL-1 and increases viability of chondrocytes Models of cartilage inflammation in horses are widely reported, and include intra-articular challenges such as lipopolysaccharide (Jacobsen et al., 2006); Freunds Complete Adjuvant (Toutain and Cester 2004) or Na-monoiodoacetate (Welch et al., 1991); or surgical disruptions including creation of osteochondral fragments (Frisbie et al., 2007), focal contusion impact injuries (Bolam et al., 2006) and ligamentous transsection (Simmons et al., 1999). While these models capably demonstrate activation of a complexity of inflammatory mechanisms within cartilage and associated subchondral bone and soft tissues, they represent a predominately traumatic inflammatory response. They are less representative of the more subtle biochemical, functional and pathophysiological changes in incipient or sub-acute articular inflammation that characterize most cases of lameness in racing horses (Steel et al., 2006).

Methods

Diets: Sasha's EQ powder was prepared in our laboratory by combining Abalone (AB), New Zealand Green Lipped Mussel (NZGLM), Shark cartilage (SC) and BO (Interpath Pty Ltd, Australia) according to the composition provided in Table 2. Sasha's EQ mixed ration (SEQ) was prepared by combining Sasha's EQ powder (10 g/kg), molasses (20 g/kg) and flavoring (Essential Sweet Horse Essence D 2344. Essentials inc. Abbotsford, BC.) (1 g/kg) to a sweet feed horse ration (Table 3), and blending in a diet mixer in 5 kg batches until fully mixed. Control ration (CON) was prepared using the same sweet feed diet blended with molasses (~20 g/kg) and flavoring (1 g/kg).

Figure 5:
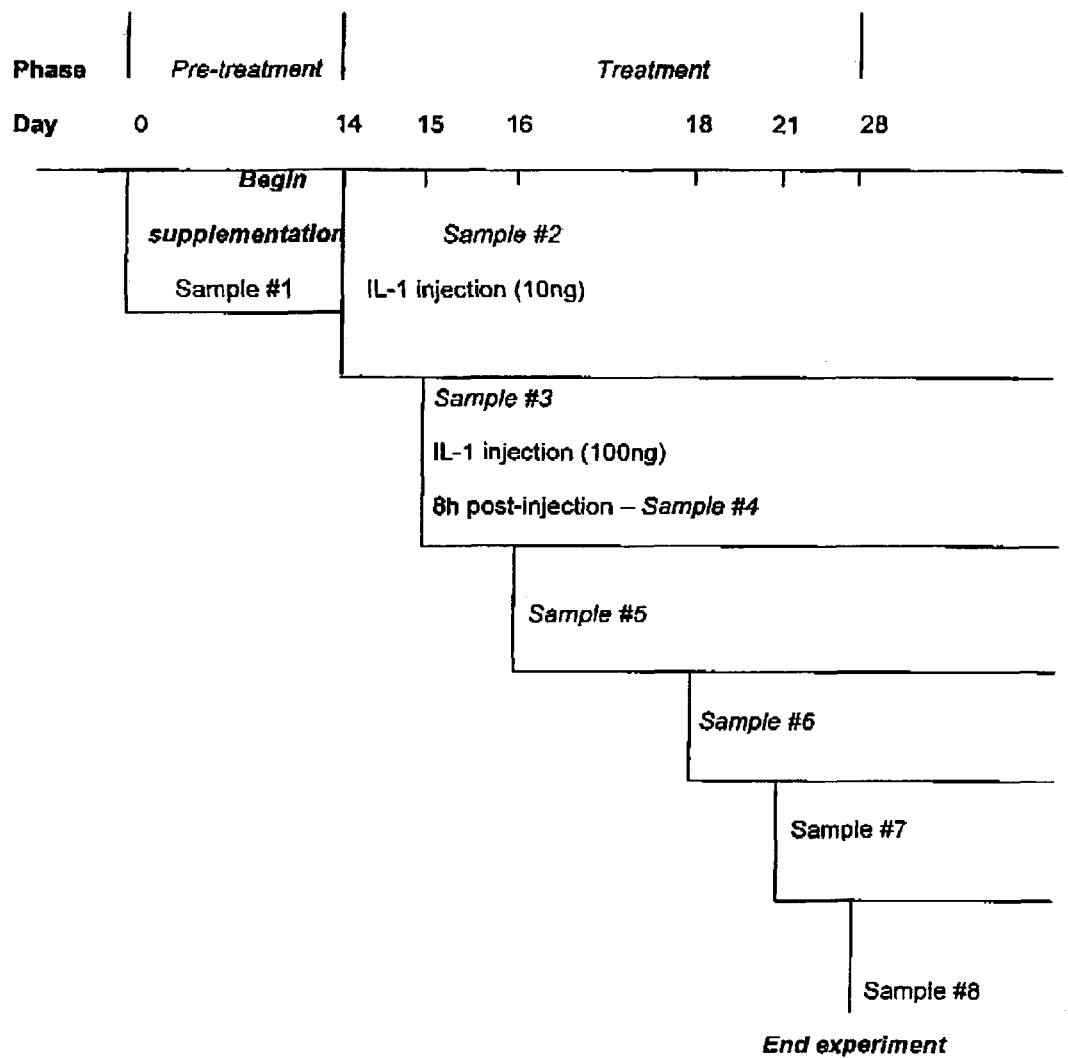
FIG. 5: Sample collection consisted of synovial fluid arthrocentesis from left and right intercarpal joints, and jugular venous blood. Dietary supplementation began on day 0 and continued for the duration of the experiment.

Horses: 11 healthy horses without signs of articular inflammation (3 thoroughbred, 8 standardbred; age 5-12 years; 10 geldings, 1 mare) were randomly allocated to either Group A (SEQ; 1.5 kg/day; n=6) or Group B (CON; 1.5 kg/day; n=5). The 28-day experiment consisted of two phases—Phase 1: pretreatment (14 days); Phase 2: treatment (14 days). Supplementation began on Day 0 and continued for the duration of the experiment (FIG. 5). Sample collection occurred on days 0 (pre), 14 (inj-1), 15 (2 samples: inj-2—taken immediately before injection; inj-2-2—taken 8 h post-injection), 16 (day 1), 18 (day 3), 21 (day 7) and 28 (day 14); on these days blood was collected from the jugular vein, and synovial fluid was sampled from both intercarpal joints by aseptic arthrocentesis (see below). An inflammatory challenge—recombinant interleukin-1β (IL-1)—was injected into the left or right intercarpal joint on day 14 (inj-1; 10 ng in 500 µL sterile saline) and 15 (inj-2; 100 ng in 500 µL sterile saline). An equal volume of sterile saline was injected into the contralateral intercarpal joint. Joint circumference as an indicator of joint effusion was measured with a tape measure at each sampling of joint fluid.

All horses were turned out in paddocks during the day and housed in box-stalls overnight. They were bedded on wood shavings and offered hay, water and mineral salts ad libitum. All procedures were approved by the University of Guelph Animal Care Committee in accordance with guidelines of the Canadian Council on Animal Care.

Arthrocentesis: The knees of both the left and right legs were shaved, and the area aseptically prepared using chlorhexadine (4%), and rinsed with 70% isopropyl alcohol. A sterile 22 gauge, 1.5" needle was inserted into the lateral aspect of the left intercarpal joint. A 3 cc sterile syringe was then attached, and approximately 1.5-2 mL of synovial fluid was aspired and immediately injected into a sterile K$_2$-heparin vacutainer. The procedure was then repeated for the right intercarpal joint. On days 14 (inj-1) and 15 (inj-2), IL-1 (500 µL) was injected into either the right or left intercarpal (500 µL saline injected into contralateral joint) after aspiration of synovial fluid and before removal of the needle hub. Approximately 1.5 mL of synovial fluid was removed from the vacutainer and placed into a microcentrifuge tube and spun at 11,000×g for 10 minutes to remove cellular debris. Supernatant was placed into another microcentrifuge tube containing 10 µg indomethacin, and frozen at −80° C. until analyzed for PGE$_2$, GAG and NO. Indomethacin was added to synovial fluid after it was collected in order to prevent further formation of PGE$_2$ during storage of samples. The remaining ~0.5 mL synovial fluid was sent to the Animal Health Laboratory (University of Guelph) for cytological analysis.

Synovial Fluid Cytology 1.0-1.5 mL of fluid was removed from the vacutainer for PGE$_2$, NO and GAG analysis (see below), and approximately 0.5 mL was analyzed for total nucleated cell count (Coulter Z2 counter; Beckman Coulter Canada Inc. Mississauga ON), protein (refractometer) and cell differential (on 100 nucleated cells) at the Animal Health Laboratory.

Synovial fluid [PGE$_2$]: Synovial fluid was thawed to room temperature then incubated with 20 µL hyaluronidase (10 mg/mL) on a tube rocker for 30 minutes at 37° C. to digest hyaluronic acid. Sample was then diluted 1:2 with formic acid (0.1%), and centrifuged 12,000×g for 10 minutes. The supernatant was decanted and analyzed for PGE$_2$ by a commercially available ELISA kit (GE Amersham, Baie D'Urfé, Québec). PGE$_2$ was extracted from the sample using provided lysis reagents to dissociate PGE$_2$ from soluble membrane receptors and binding proteins, and then quantified according to kit protocol. Plates were read using a Victor 3 microplate reader (Perkin Elmer, Woodbridge ON) with absorbance set at 450 nm. A best-fit $3^{rd}$ order polynomial standard curve was developed for each plate ($R^2 \geq 0.99$), and these equations were used to calculate PGE$_2$ concentrations for samples from each plate.

Synovial fluid [GAG]: Hyaluronic acid in synovial fluid samples were digested with hyaluronidase as described above. GAG concentration of synovial fluid was determined using a 1,9-DMB spectrophotometric assay as described by Chandrasekhar et al. (1987). Samples were diluted 1:3 with dilution buffer and placed into a 96-well microtitre plate. Guanidine hydrochloride (275 g/L) was added to each well followed immediately by addition of 150 µL DMB reagent. Plates were incubated in the dark for 10 minutes, and absorbance was read on a Victor 3 microplate reader at 530 nm. Sample absorbance was compared to that of a bovine chondroitin sulfate standard (Sigma, Oakville ON). A best-fit linear standard curve was developed for each plate ($R^2 \geq 0.99$), and these equations were used to calculate GAG concentrations for samples on each plate.

Synovial fluid [NO]: Nitrite ($NO_2^-$), a stable oxidation product of NO, was analyzed by the Griess reaction (Fenton et al., 2002). Undiluted TCM samples were added to 96 well plates. Sulfanilamide (0.01 g/mL) and N-(1)-Napthylethylene diamine hydrochloride (1 mg/mL) dissolved in phosphoric acid (0.085 g/L) was added to all wells, and absorbance was read within 5 minutes on a Victor 3 microplate reader at 530 nm. Sample absorbance was compared to a sodium nitrite standard.

Data Analysis and Presentation

Two-way repeated measures (RM) analysis of variance (ANOVA) was used to detect differences between treatments. When a significant F-ratio was obtained, the Holm Sidak post-hoc test was used to identify differences between treatments. One-way RM ANOVA was used to detect differences within treatments with respect to time. For blood and synovial fluid data, one-way comparisons of data were made against pre- and inj-1 data, as each represented baseline for diet and IL-1 injections, respectively. Data are presented as means±SEM. Graphs for biochemistry and hematology data are scaled to physiological reference intervals unless otherwise stated. Reference intervals are those published by the Animal Health Laboratory, University of Guelph (http://www.labservices.uoguelph.ca/units/ahl/files/AHL-user-guide.pdf).

Results

Figure 7:
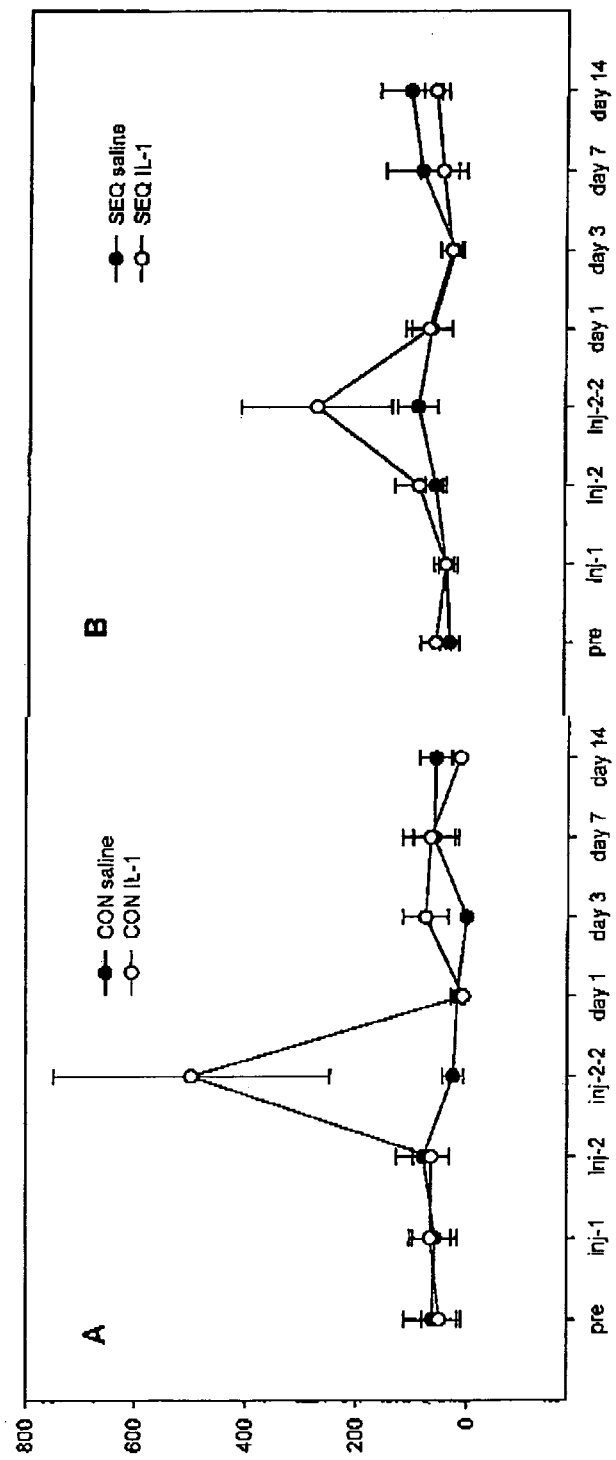
FIG. 7: Synovial fluid [$PGE_2$] from intercarpal joints of control horses injected with IL-1 (10 ng on inj-1, 100 ng on inj-2) or saline in CON (A) and SEQ (B) horses. Healthy horses received a diet containing placebo (CON) or Sasha's EQ (SEQ) for 28 days. Intra-articular IL-1 (10 ng in 500 µL sterile saline) was injected into the intercarpal joint, and sterile saline (500 µL) was injected into the contralateral joint 14 days after commencement of supplementation (inj-1). A second intra-articular injection of IL-1 (100 ng in 500 µL sterile saline) or saline (500 µL) was injected the same joints 24 h later (inj-2). Approximately 1.5 mL synovial fluid was aspirated from the intercarpal joints on days pro (before commencement of supplementation), inj-1 and inj-2 (prior to injections), inj-2-2 (8 h after $2^{nd}$ IL-1 injection), and 1, 3, 7 and 14 days after $2^{nd}$ IL-1 injection. * denotes significant change from inj-1 within treatments. Letters denote significant differences between saline and IL-1 within treatments. Changes are significant when $p \leq 0.05$.

Synovial Fluid $PGE_2$:

CON horses: There was no significant change in synovial fluid [$PGE_2$] in saline-injected joints at any time (FIG. 7, A). Relative to pre-injection concentrations, [$PGE_2$] was significantly increased at inj-2-2 (321.3±161.8 pg/mL; p=0.04) in IL-1-injected joints, at which time synovial fluid [$PGE_2$] was significantly higher in IL-1-injected joints than in saline-injected joints (p<0.001).

SEQ horses: Data represent n=5, as one outlier horse was removed from the analysis. $PGE_2$ did not change in saline-injected joints of SEQ horses. Like CON horses, there was a spike in [$PGE_2$] increased at inj-2-2 (175.4±89.2 pg/mL) in IL-1-injected joints of SEQ horses (FIG. 7, B). However, this increase was not significant when compared with pre-injection concentrations (p>0.05). $PGE_2$ response to saline injection was not different in SEQ horses compared with CON horses. There was no significant difference in $PGE_2$ response to IL-1 injection compared with saline in SEQ horses.

Although mean [$PGE_2$] at inj-2-2 in SEQ horses was approximately 55% that of CON horses, variability about the means resulted in no significant difference between diets.

Figure 8:
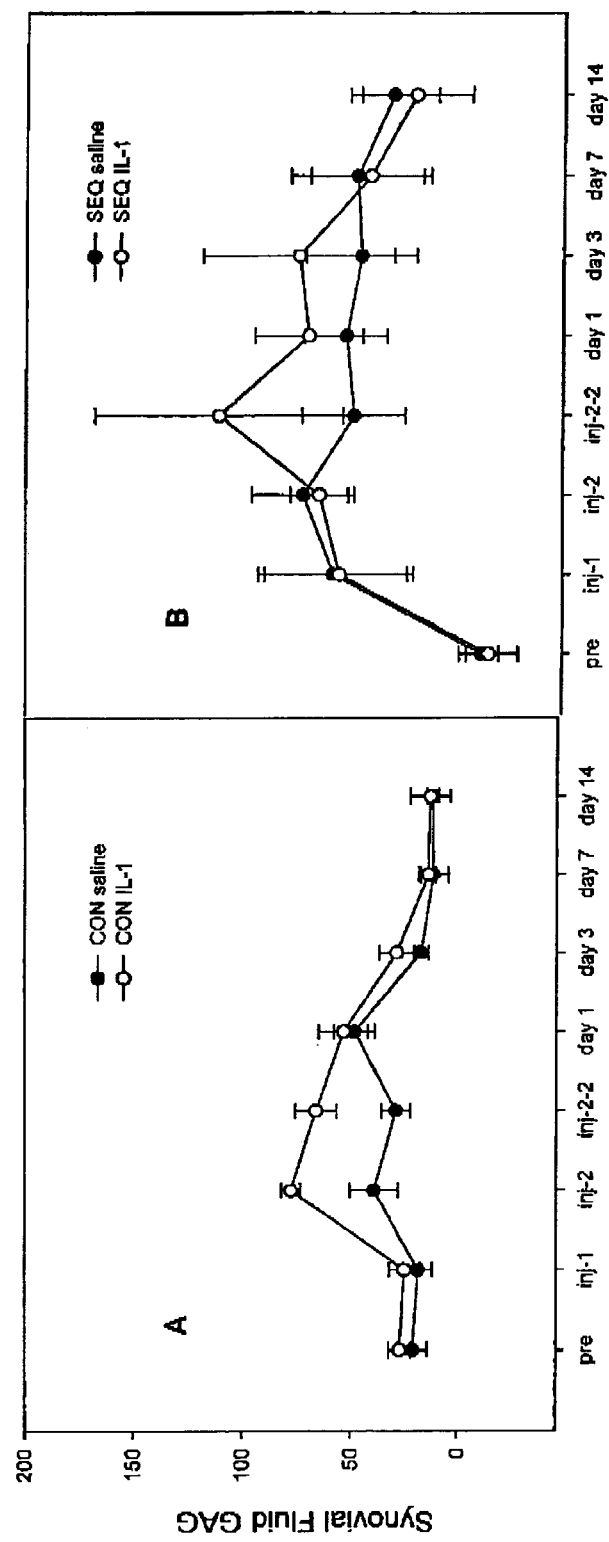
FIG. 8: Synovial fluid [GAG] from intercarpal joints injected with IL-1 (10 ng on inj-1, 100 ng on inj-2) or saline in CON (A) and SEQ (B) horses. Healthy horses received a diet containing placebo (CON) or Sasha's EQ (SEQ) for 28 days. Intra-articular IL-1 (10 ng in 500 µL sterile saline) was injected into the intercarpal joint, and sterile saline (500 µL) was injected into the contralateral joint 14 days after commencement of supplementation (inj-1). A second intra-articular injection of IL-1 (100 ng in 500 µL sterile saline) or saline (500 µL) was injected the same joints 24 h later (inj-2). Approximately 1.5 mL synovial fluid was aspirated from the intercarpal joints on days pre (before commencement of supplementation), inj-1 and inj-2 (prior to injections), inj-2-2 (8 h after $2^{nd}$ L-1 injection), and 1, 3, 7 and 14 days after $2^{nd}$ IL-1 injection. * denotes significant change from inj-1 within treatments. Letters denote significant difference between IL-1 and saline within treatments. SEQ horses had significantly higher synovial fluid [GAG] than CON horses. Differences were significant when $p \leq 0.05$.

GAG:

CON horses: Synovial fluid [GAG] increased in saline-injected joints between inj-1 (18.3±6.8 μg/mL) and day 1 (48.1±9.6 μg/mL) (FIG. 8, A). Injection of IL-1 (10 ng) caused a rapid and significant increase in synovial fluid [GAG] between inj-1 (24.5±7.3 μg/mL) and inj-2 (77.6±4.4 μg/mL). Synovial fluid [GAG] remained significantly elevated in IL-1-injected joints at inj-2-2 (66.0±9.6 μg/mL) and day 1 (53.3±11.4 μg/mL) compared with pre-injection concentrations. The magnitude of increase in synovial fluid [GAG] was significantly higher in IL-1-injected joints than in saline-injected joints (p=0.003).

SEQ horses: Synovial fluid [GAG] tended to increase (p=0.09) in both saline- and IL-1-injected joints between pre (saline: 29.3±5.9 μg/mL; IL-1: 27.0±10.8 μg/mL) and inj-1 (saline: 85.5±28.0 μg/mL; IL-1: 83.2±27.9 μg/mL), suggesting an effect of diet on synovial fluid [GAG] (FIG. 8, B). There was no change in synovial fluid [GAG] in saline- or IL-1-injected joints over the course of the experiment. There was no significant difference in synovial fluid [GAG] of IL-1-injected and saline-injected joints.

Synovial fluid [GAG] in IL-1- and saline-injected joints was significantly higher in SEQ horses than CON horses (p<0.001). This difference was most likely an effect of diet, and not an effect of IL-1, as evidenced by the fact that the majority of the increase occurred prior to any IL-1 injection.

NO:

CON horses: Synovial fluid [NO] was low and variable over the course of the experiment in both saline- and IL-1-injected joints. There was no significant effect of either saline or IL-1 injection on NO levels in CON horses over time. The magnitude of synovial fluid [NO] was not different between IL-1- and saline-injected joints.

SEQ horses: There was no change in synovial fluid [NO] in IL-1- or saline-injected joints at any time over the course of the experiment. There was no significant in difference between IL-1 or saline at any time.

There was no significant effect of diet on synovial fluid [NO] in IL-1- or saline-injected joints.

Synovial Fluid Cytology:

CON horses: Pre-injection total cell count (0.61±0.1×$10^9$/L) was significantly elevated by provision of exogenous IL-1 (10 ng) at inj-2 (40.17±16.1×$10^9$/L). Cell count was not further increased following the $2^{nd}$ IL-1 injection (100 ng), but remained slightly (but not significantly) elevated through day 1. Inj-1 cell count in saline-injected joints (0.6±0.2×$10^9$/L) increased mildly, reaching a maximum at day 1 (6.0±2.6×$10^9$/L), but this increase was not significant. Total cell counts of saline- and IL-1 injected joints were significantly different from each other at inj-2 [i.e., 24 h after the $1^{st}$ IL-1 injection (10 ng)]. The increase in cell count was due mainly to an increase in the relative percentage of neutrophils. Percent neutrophils significantly increased in both IL-1- and saline-injected joints after the first injection. Neutrophil counts significantly declined in both IL-1- and saline-injected joints between day 1 and 3 without further increase for the remainder of the experiment. There was no difference in % neutrophils between IL-1- and saline-injected joints.

SEQ horses: Pre-injection total cell count (0.4±0.03×$10^9$/L) was significantly elevated by provision of exogenous IL-1 (10 ng) by inj-2 (27.5±8.7×$10^9$/L). Cell count was not further increased by inj-2-2, but remained significantly elevated through day 1. Inj-1 total cell count in saline-injected joints (0.4±0.1×$10^9$/L) increased mildly, reaching a maximum at inj-2-2 (4.0±2.6×$10^9$/L), but this increase was not significant. Total cell counts of saline- and IL-1 injected joints were significantly different from each other at inj-2 (ie. 24 h after the $1^{st}$ IL-1 injection of 10 ng), inj-2-2 (ie. 8 h after the $2^{nd}$ IL-1 injection of 100 ng), and day 1 (ie. 24 h after the $2^{nd}$ IL-1 injection of 100 ng). Percent neutrophils significantly increased in both IL-1- and saline-injected joints after the first injection. Increase in neutrophil concentration of saline-injected joints may have been attributable to minor inflammation being caused by injection trauma. Neutrophil counts (%) significantly declined in both IL-1- and saline-injected joints between day 1 and 3 with a second significant spike on day 7. There was no difference in % neutrophils between IL-1- and saline-injected joints.

There was no significant difference in the effect of SEQ and CON diets on total cells counts or % neutrophils in IL-1- or saline-injected joints.

CON horses: Synovial fluid [protein] was significantly increased by injection of 10 ng IL-1 (20±0.0 g/L to 39.4±4.0 g/L) (FIG. 9, A). [Protein] was not further increased by injection of 100 ng IL-1, and significantly declined 24 h after the 100 ng injection. Injection of saline also resulted in a significant increase in [protein] immediately after the first injection, returning to baseline concentrations by day 1 (25.5±1.5 g/L). The magnitude of increase in [protein] over the course of the experiment was significantly higher in IL-1-injected than saline-injected joints (p=0.01).

Figure 9:
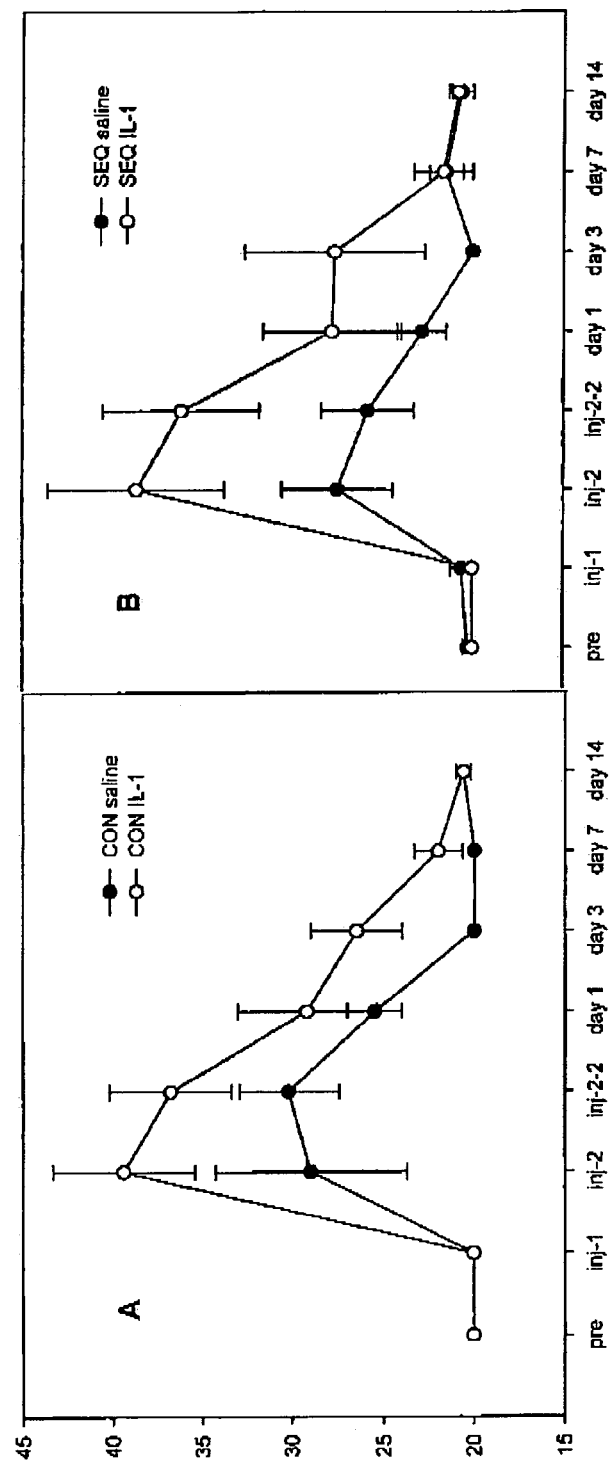
FIG. 9: Synovial fluid [protein] from intercarpal joints of control horses injected with IL-1 (10 ng on inj-1, 100 ng on inj-2) or saline in CON (A) and SEQ (B) horses. Healthy horses received a diet containing placebo (CON) or Sasha's EQ (SEQ) for 28 days. Intra-articular IL-1 (10 ng in 500 µL sterile saline) was injected into the intercarpal joint, and sterile saline (500 µL) was injected into the contralateral joint 14 days after commencement of supplementation (inj-1). A second intra-articular injection of IL-1 (100 ng in 500 µL sterile saline) or saline (500 µL) was injected the same joints 24 h later (inj-2). Approximately 1.5 mL synovial fluid was aspirated from the intercarpal joints on clays pre (before commencement of supplementation), inj-1 and inj-2 (prior to injections), inj-2-2 (8 h after $2^{nd}$ IL-1 injection), and 1, 3, 7 and 14 days after $2^{nd}$ IL-1 injection. * denotes significant change from inj-1 within treatments. Letters denote significant differences between IL-1 and saline within treatments. Differences were significant when $p \leq 0.05$.

SEQ horses: Injection of 10 ng IL-1 resulted in a significant increase in synovial fluid protein on inj-2 (38.7±4.9 g/L), inj-2-2 (36.2±4.4 g/L), and day 1 (27.8±3.8 g/L) compared with inj-1 (20±0 g/L) (FIG. 9, B). There was no further effect of the $2^{nd}$ IL-1 injection of 100 ng on [protein]. Saline injection also resulted in a significant increase in [protein] on inj-2-am (27.5±3.0 g/L) and inj-2-pm (25.8±2.5 g/L) compared with inj-1 (20.6±0.6 g/L). The magnitude of increase in synovial fluid [protein] was significantly higher in IL-1-injected joints than in saline-injected joints (p=0.003).

There was no significant difference in the effect of SEQ and CON diets on synovial fluid [protein] in IL-1- or saline injected joints.

Figure 6:
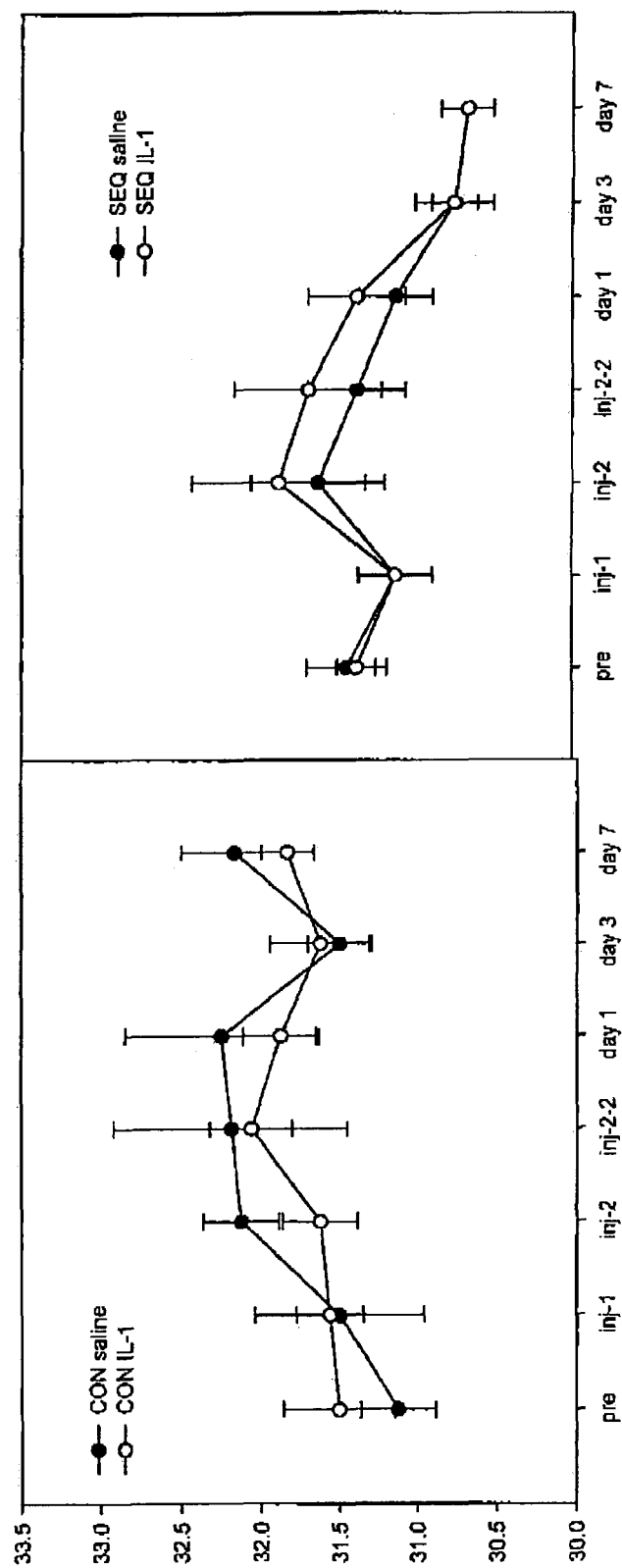
FIG. 6: Circumference of intercarpal joints injected with IL-1 (10 ng on inj-1, 100 ng on inj-2) or saline in CON (A) and SEQ (B) horses. Healthy horses received a diet containing placebo (CON) or Sasha's EQ (SEQ) for 28 days. Intra-articular IL-1 (10 ng in 500 μL sterile saline) was injected into the intercarpal joint, and sterile saline (500 μL) was injected into the contralateral joint 14 days after commencement of supplementation (inj-1). A second intra-articular injection of IL-1 (100 ng in 500 μL sterile saline) or saline (500 μL) was injected the same joints 24 h later (inj-2). Approximately 1.5 mL synovial fluid was aspirated from the intercarpal joints on days pre (before commencement of supplementation), inj-1 and inj-2 (prior to injections), inj-2-2 (8 h after $2^{nd}$ IL-1 injection), and 1, 3, 7 and 14 days after $2^{nd}$ IL-1 injection. * denotes significant change from inj-1 within treatments. Letters denote significant differences between IL-1 and saline within treatments. Joint circumference of IL-1-injected joints was significantly lower in SEQ horses than CON horses ($p<0.001$). Differences were significant when $p \leq 0.05$.

Joint Circumference:

CON horses: There was no significant change in circumference over time in IL-1- or saline-injected joints, and there was no significant difference in joint circumference between IL-1- and saline-injected joints (FIG. 6, A).

SEQ horses: There was a significant increase in joint circumference in IL-1-injected joints between inj-1 (31.1±0.2 cm) and inj-2 (31.9±0.5 cm) in SEQ horses (FIG. 6, B). Joint circumference remained significantly elevated at inj-2-2 (31.7±0.4 cm) before declining to pre-injection levels. Exactly the same pattern was shown in the saline-injected joints of SEQ horses.

Joint circumference of IL-1-injected joints was significantly lower in SEQ horses than CON horses (p<0.001).

Fractionation of *Biota* Oil

Chromatography

Oil from the seeds of *Biota Orientalis* was fractionated using an Agilent 1200 Preparative HPLC equipped with a diode array detector and an automated fraction collector. The column used was an Agilent Prep C18, 10 μm (30×250 mm) with the following gradient at a flow rate of 20 ml/minute with a 900 μL injection of Constituent 4. 0-5 minutes 80% water 20% Acetonitrile. 5-7 minutes Gradient change to 10% water 90% Acetonitrile, 7-25 minutes isocratic 10% water 90% Acetonitrile. Fraction detection was achieved at 254 nm.

Figure 13:
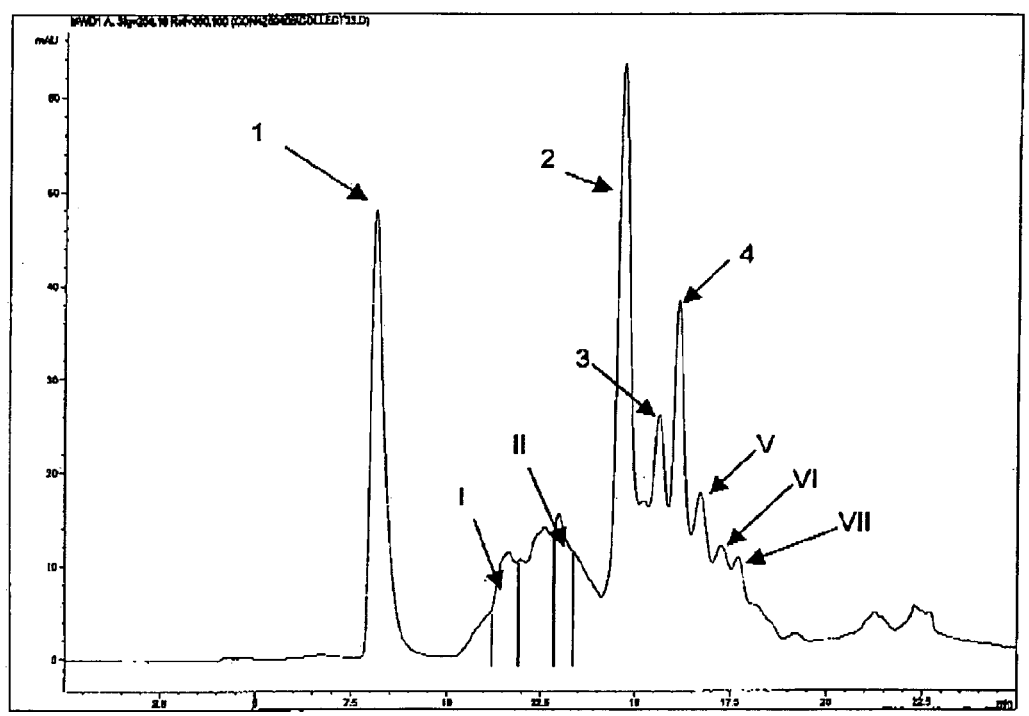
FIG. 13: Chromatographic spectrum of the extract of *Biota orientalis* oil.

Mass Spectrometry:

The mass spectrometry detection was performed on an Agilent 6210 MSD Time of Flight mass spectrometry in both positive and negative ion mode. The following electrospray ionization conditions were used, drying gas: nitrogen (7 mL min−1, 350° C.); nebuliser gas: nitrogen (15 psi); capillary voltage: 4.0 kV; vaporization temperature: 350° C. and cone voltage: 60V FIG. 13 shows the chromatographic spectrum of the oil, and various fractions were collected and numbered as shown.

Chondroprotective/Chondrogenic Potential of Fractions from *Biota* Oil

A total of ten fractions (Fr1, Fr2, Fr3, Fr4, Fri, Frii, FrV, FrVi and FrVii) were tested in vitro. Clonetics® Normal Human Articular Chondrocytes (NHAC-knee) obtained from Lonza Australia Pty Ltd, were grown in chondrocyte growth medium (CGM) supplemented with growth factors. NHACs were used at passage #3-4 for all experiments.

Fraction 1 was water soluble, Fractions 2-10 dissolved at a final concentration of 64 mg/ml in cell culture grade Dimethylsulhpoxide (DMSO). NHAC Cells were grown in the presence or absence of above mentioned fractions for 24, 48 hours and effects on the morphology were observed during the treatment. The following assays were carried out using the protocols as per kit instructions:

Viability/cytotoxicity
   Cytotoxicity (Lactate Dehydrogenase) assay (Roche Applied Science)

Cell Growth and Proliferation:
   BrdU labeling and detection kit III (Roche Applied Science)
   CyQUANT cell proliferation assay kit (Molecular Probes: Invitrogen)

Apoptosis/Necrosis
   Apoptotic DNA ladder extraction kit (Biovision)
   Annexin-V-Flous Kit (Roche Applied Science)

Observations of the effect on chondrocyte morphology following treatment with the various fractions revealed that Fraction 1, even at the highest concentration (128 μg/ml) tested, preserved the normal cell morphology and helped in cell growth maintenance. Other fractions caused apoptotic and necrotic morphology at higher concentrations (128-32 μg/ml) leading to dislodgement of adherent cells and cell death.

Fraction 1 showed no cytotoxicity towards NHACs even at the highest concentration (128 μg/ml) tested. At highest concentration all other fractions were cytotoxic. However Fr V, Fr Vi and Fr i showed low cytotoxicity towards NHACs at ≦64 μg/ml.

Very low (in the normal range) cell apoptosis and necrosis, was observed in chondrocytes treated with Fr 1, Fr i, and Fr V.

Figure 14:
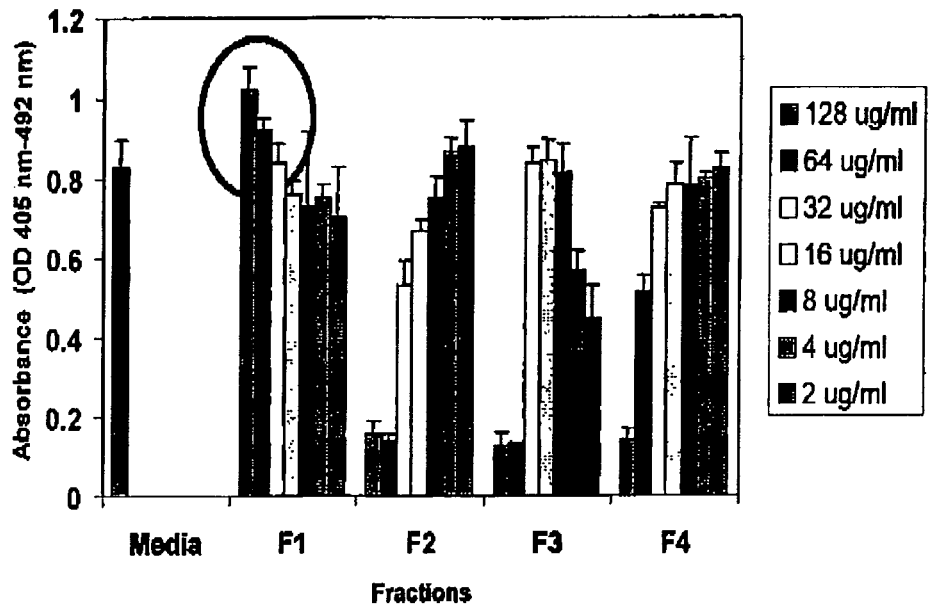
FIG. 14: Shows the BrdU cell proliferation assay of fractions F1, F2, F3 and F4.
Figure 15:
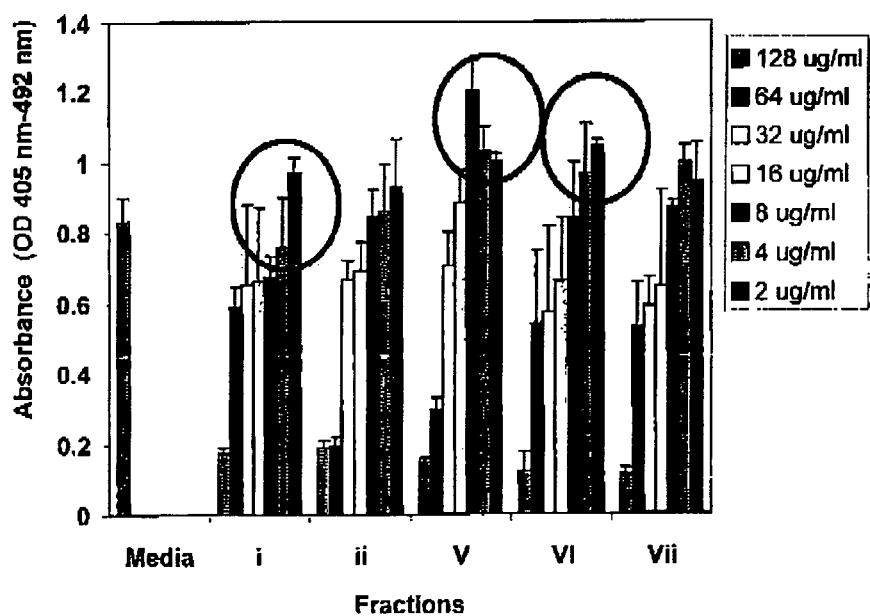
FIG. 15: Shows the BrdU cell proliferation assay of fractions I, ii, V, Vi and Vii.

In BrdU cell proliferation assay, Fraction 1 significantly enhanced the NHACs proliferation in a dose dependent manner. Other fractions significantly stimulated cell proliferation at conc≦8 μg/ml but were cytotoxic at higher concentrations (FIGS. 14 and 15).

Fraction 1 was found to be water soluble and was further investigated and shown to contain five separate components by analytical chromatography. Structural elucidation then identified each of these compounds as follows:

| | |
|---|---|
| F1.1 | (9Z,13S,15Z)-12,13-epoxyoctadeca-9,11,15-trienoic acid |
| F1.2a | cis,cis,cis-9,12,15-octadecatrienoic acid (ALA); |
| F1.2b | cis,cis,cis-6,9,12-octadecatrienoic acid (GLA); and |
| F1.3 | cis,cis-9,12-octadecadienoic acid; |
| F1.4 | 9-Octadecenoic acid |

Each of the above fractions was then individually assayed again for viability/cytotoxicity, cell growth and proliferation, apoptosis/necrosis using the tests as previously mentioned.

Each of the Fractions 1.1-1.4 were found to be soluble in water and showed no cytotoxicity. In addition, there was no significant difference between the apoptotic index (A/I) and necrotic index (Necrotic index (N/I) of treated compared to non-treated cells, all were below 10 units.

Figure 16:
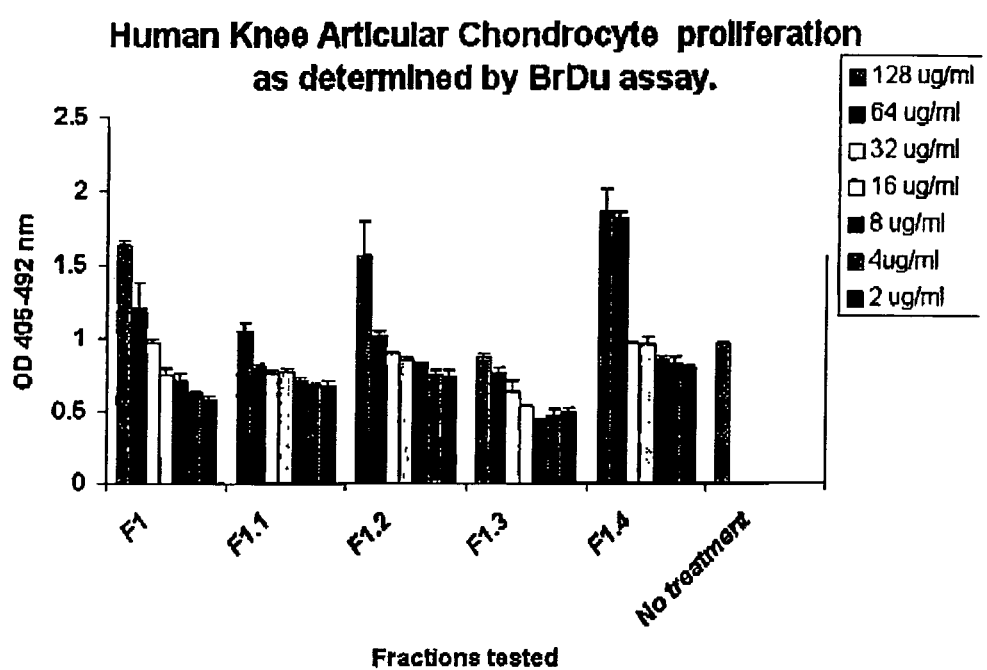
FIG. 16: Shows the BrdU cell proliferation assay of fractions F1, F1-1, F1.2, F1.3 and F1.4.

FIG. 16 shows the level of chondrocyte proliferation for F1.1-1.4 under BrDu assay conditions, and F1.4 is the most active in relation to cell growth. The level of activity of the combined fractions, labeled as F1 are also shown.

The fractions F1.1-1.4, and the combined fraction F1, have be shown to exhibit high efficacy in increasing human knee chondrocyte proliferation Discussion These data present evidence for a minimally invasive, reversible model of early stage articular inflammation that can be used to evaluate putative anti-inflammatory nutraceuticals. IL-1 was chosen as the intra-articular challenge due to its central role in propagating the inflammatory response in arthritis (Jacques et al., 2006); and $PGE_2$ was selected as the primary dependent variable due to its importance in regulation of matrix metabolism (Pavlovic et al., 2006). In order to establish a sampling schedule, the time course of $PGE_2$ production subsequent to intra-articular injection of IL-1 was investigated. A maximal $PGE_2$ response at approximately 8 h after injection was predicted based on evidence that intra-articular [IL-1] is maximally elevated in equine to synovial fluid at approximately 4 h after provision of exogenous IL-1 (Hardy et al., 1998). $PGE_2$ is subsequently elevated at approximately 6 h (Sedgewick and Lees 1986). It was predicted, therefore, that an 8 h sample would provide a reasonable estimation of a maximal increase in synovial fluid $[PGE_2]$.

The initial 10 ng injection provided to the horses was far in excess of the concentration of IL-1 known to be associated with joint disease in horses ($\cong$4.5 pg/mL; Bertone et al., 2001) and was expected to produce a significant $PGE_2$ response. However, though effective in initiating primary recruitment of inflammatory cells to the joint space and elevating synovial fluid [GAG], it was demonstrated that a single IL-1 injection of 10 ng resulted in a poor 8 h $PGE_2$ response. This may be attributed, at least in part, to species-specific differences in the protein structure of IL-1 and its interaction with target tissues. The protein sequence of human IL-β (LOCUS CAG28607; Ebert et al., 2004) shares only 66% identity with equine IL-1 (LOCUS Q28386; Kato et al., 1995), providing some explanation for why equine tissue may be less sensitive to stimulation with human IL-1 than with equine IL-1. It is reported that provision of 175 ng of exogenous intra-articular recombinant human IL-1β results in an acute inflammatory response in isolated limb preparations of horses (Hardy et al., 1998). In an effort to limit the inflammatory response to a subclinical magnitude, a 'priming' IL-1 dose was injected in order to establish expression of IL-1 receptors on chondrocytes and synoviocytes, and followed by a second 'challenge' so IL-1 dose lower than 175 ng to produce a significant $PGE_2$ response.

The double IL-1 injection protocol resulted in a statistically significant increase in $PGE_2$ at 8 h after the $2^{nd}$ injection. None of the CON horses were overtly lame at the walk or brief trot at any time during the experiment, despite mean peak synovial fluid $[PGE_2]$ (498 pg/mL) being commensurate with that associated with lameness in horses (488 pg/mL; de Grauw et at, 2006). The increase in $PGE_2$ was not accompanied by a concomitant increase in NO. This provides a possible explanation as to why these horses were not lame, as transmission and perception of nociceptive pain occurs predominately as a result of combined effect of elevated $PGE_2$ and NO. CON horses may have demonstrated a low-grade lameness had they been subjected to moderate exercise, but this was not undertaken due to the confounding effect of exercise on synovial fluid $[PGE_2]$ (van den Boom et al., 2005). The observed increase in synovial fluid $[PGE_2]$ in CON horses provides good evidence for a low-grade IL-1-induced inflammation within the joint.

Trafficking of inflammatory cells and release of glycosaminoglycan into the synovial fluid were more sensitive to stimulation with IL-1 than production of $PGE_2$, as an increase in synovial fluid [GAG] and [neutrophils] was observed 24 h after the initial 10 ng IL-1 injection. Synovial fluid [protein] was also elevated immediately after the $1^{st}$ IL-1 injection. These parameters were not further increased by provision of a higher IL-1 challenge. These responses are consistent with a 'pre-arthritic' inflammatory state (Adarichev et al., 2006). Genes turned on in the early stage of arthritis are predominately those associated with transcription of chemokines, cytokines (notably, IL-1), and metalloproteinases, notably, MMP-13 and MMP-9. Chemokines are potent signals for inflammatory cell migration into the synovial space. As synoviocytes and endothelial cells of the synovial membrane become activated to express cell adhesion molecules and produce chemokines, neutrophil extravasation into the joint space greatly increases, as was observed in our study as a steep increase in synovial fluid [neutrophils]. Cells of the synovial membrane also become more permeable to serum proteins (Middleton et al., 2004) resulting in the observed rapid increase in synovial fluid [protein]. MMP-13 (Yammani et al., 2006) and MMP-9 (Soder et al., 2006) are key degradative enzymes in articular cartilage, and the increase in IL-1-induced synovial fluid [GAG] observed in the current study support studies demonstrating substantial upregulation of genes encoding these enzymes in early arthritis (Adarichev et al., 2006; Kydd et al., 2007). Micro-array analysis of pre-arthritic cartilage in PG-stimulated mice revealed that genes encoding for phospholipase $C_2$, the enzyme catalyzing release of arachidonic acid from nuclear membranes, was not elevated (Adarichev et al., 2006). This may explain, at least in part, why $PGE_2$ required a longer time course for elevation subsequent to IL-1 stimulation than cell migration and release of GAGS.

Intra-articular challenge with IL-1 did not result in a consistent increase in synovial fluid NO. IL-1-induced NO has been frequently reported in cartilage explant models (Pearson et al., 2007; Petrov et al. 2005), cells taken from animal models of acute articular inflammation (Kumar et al., 2005) and clinical cases of articular inflammation (Karatay et al., 2005). The data described herein provide support for evidence that genes encoding inducible NO synthase are not upregulated in early stage arthritis (Kydd et al., 2007), which delays IL-1-induced formation of NO.

Sasha's EQ provided protection to IL-1-stimulated joints as evidenced by: 1) no significant increase in synovial fluid $[PGE_2]$; 2) increased [GAG] in the synovial fluid prior to IL-1 challenge, then preventing IL-1-induced increase in GAG; and 3) limited effusion into the joint space subsequent to IL-1 challenge. This product was selected is as the test nutraceutical due to recent evidence that its individual ingredients significantly reduce $PGE_2$, GAG release and NO production in cartilage explants (Pearson et al., 2007). As part of the diet for 2 weeks prior to an intra-articular IL-1 challenge, SEQ prevented significant elevation in IL-1-induced $PGE_2$. Similar to CON horses, $PGE_2$ response to IL-1 in SEQ horses peaked at 8 h after the second IL-1 injection, but the peak was lower, and did not result in statistically significant changes over time or significant differences between IL-1 and saline injection. This provides evidence for the potential for SEQ to reduce inflammation and pain associated with elevated $PGE_2$ in horses with early stage arthritis, and implies that feeding SEQ to horses prior to articular damage may impede progression of the disease to a more advanced stage.

The observed increase in synovial fluid [GAG] of SEQ horses in both saline- and IL-1-injected joints between pre and inj-1—ie. before inflammatory challenge—provides evidence for the post-absorptive accumulation of dietary GAGS within the synovial space. It would be of value to quantify plasma [GAG] after dietary provision of SEQ in order to determine whether GAGs from SEQ are preferentially sequestered into the synovial space, or are evenly distributed throughout the body of the animal. Of importance is the lack of significant increase in [GAG] subsequent to challenge with IL-1, providing support for a chondroprotective role of SEQ in horses with early stage arthritis. As metalloproteinases 13 and 9 are rapidly and substantially upregulated in early stage arthritis (Adarichev et al., 2006; Kydd et al., 2007), the action of SEQ on enzyme activity and/or production of enzyme protein, and also on the expression/activity of aggrecanases would provide useful information on a possible mechanism of chondroprotective action.

The effectiveness of Sasha's EQ in preventing biochemical indicators of early-stage arthritis likely results from a combined effect of its 4 ingredients. A previous study showed that a simulated digest of NZGLM and SC is effective in inhibiting IL-1-induced $PGE_2$ production in cartilage explants (Pearson et al., 2007). This study also showed that SC significantly increased media [GAG] through provision of exogenous GAGS, and NZGLM prevented IL-1-induced release of GAGs from the cartilage matrix. These data support those of other authors who report significant improvement in arthritic signs in dogs provided with dietary NZGLM (Pollard et al., 2006), and significant protection by glucosamine and chondroitin—the major bioactive constituents of SC—of cartilage explants against degradation by IL-1 (Dechant et al., 2005).

The effectiveness of the biota oil extract F1.2-1.4 and F1 in increasing chondrocyte cell proliferation in human knee cartilage has until now not been known. The use of the compounds of F1.1-1.4 either separately or as a mixture with one or more of the other fractions provides for a remarkable improvement in the treatment of conditions, such as osteoarthritis.

Any improvement may be made in part or all of the method steps and systems components. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

REFERENCES

Adarichev V A, Vermes C, Hanyecz A, Ludanyi K, Tunyogi-Csapo M, Finnegan A, Mikecz K, Giant T T. (2006) Antigen-induced differential gene expression in lymphocytes and gene expression profile in synovium prior to the onset of arthritis. Autoimmunity; 39(8):663-73.

Akarasereenont P, Techatrisak K, Chotewuttakorn S, Thaworn A. (1999) The induction of cyclooxygenase-2 in IL-1beta-treated endothelial cells is inhibited by prostaglandin E2 through cAMP. Mediators Inflamm; 8(6):287-94.

Aoyama T. Liang B, Okamoto T, Matsusaki T, Nishijo K, Ishibe T, Yasura K, Nagayama S, Nakayama T, Nakamura T, Toguchida J. (2005) PGE2 signal through EP2 promotes the growth of articular chondrocytes. J Bone Miner Res; 20(3):377-89.

Bolam C J, Hurtig M B, Cruz A, McEwen B J. (2006) Characterization of experimentally induced post-traumatic osteoarthritis in the medial femorotibial joint of horses. Am J Vet Res; 67(3):433-47.

Brochhausen C, Neuland P, Kirkpatrick C J, Nusing R M, Klaus G. (2006) Cyclooxygenases and prostaglandin E2 receptors in growth plate chondrocytes in vitro and in situ—prostaglandin E2 dependent proliferation of growth plate chondrocytes. Arthritis Res Ther; 8(3):R78 [Epub ahead of print]

Bui L M, Bierer T L. (2003) Influence of green lipped mussels (Perna canaliculus) in alleviating signs of arthritis in dogs. Vet Ther; 4(4):397-407.

Chan P S, Caron J P, Rosa G J, Orth M W. (2005) Glucosamine and chondroitin sulfate regulate gene expression and synthesis of nitric oxide and prostaglandin E(2) in articular cartilage explants. Osteoarthritis Cartilage; 13(5): 387-94.

Chandrasekhar S, Esterman M A, Hoffman H A. (1987) Microdetermination of proteoglycans and glycosaminoglycans in the presence of guanidine hydrochloride. Anal Biochem; 161(1):103-108.

Dechant J E, Baxter G M, Frisbie D D, Trotter G W, McIlwraith C W. (2005) Effects of glucosamine hydrochloride and chondroitin sulphate, alone and in combination, on normal and interleukin-1 conditioned equine articular cartilage explant metabolism, Equine Vet J, 37, 227-31.

de Grauw J C, van de Lest C H, van Weeren R, Brommer H, Drama P A. (2006) Arthrogenic lameness of the fetlock: synovial fluid markers of inflammation and cartilage turnover in relation to clinical joint pain. Equine Vet J; 38(4): 305-11.

Del Toro F Jr, Sylvia V L, Schubkegel S R. Campos R, Dean D D, Boyan B D, Schwartz Z. (2000) Characterization of prostaglandin E(2) receptors and their role in 24,25-(OH)(2)D(3)-mediated effects on resting zone chondrocytes. J Cell Physiol; 182(2):196-208.

Duke J A, Ayensu E S. Medicinal Plants of China Reference Publications, Inc. (1985) ISBN 0-917256-20-4

Ebert L, Schick M, Neubert P, Schatten R, Henze S, Korn B. Direct Submission (7 May 2004) RZPD Deutsches Ressourcenzentrum fuer Genomforschung GmbH Im Neuenheimer Feld 580; D-69120 Heidelberg, Germany Fehrenbacher A, Steck E, Rickert M, Roth W, Richter W. (2003) Rapid regulation of collagen but not metalloproteinase 1, 3, 13, 14 and tissue inhibitor of metalloproteinase 1, 2, 3 expression in response to mechanical loading of cartilage explants in vitro. Arch Biochem Biophys; 410(1): 39-47

Frisbie D D, Kawcak C E, Werpy N M, Park R D, McIlwraith C W. (2007) Clinical, biochemical, and histologic effects of intra-articular administration of autologous conditioned serum in horses with experimentally induced osteoarthritis. Am J Vet Res; 68(3):290-6.

Green D M, Noble P G, Ahuero J S, Birdsall H H. (2006) Cellular events leading to chondrocyte death after cartilage impact injury. Arthritis Rheum; 54(5):1509-17.

Hardy J, Bertone A L, Weisbrode S E, Muir W W, O'Dorisio T M, Masty J. (1998) Cell trafficking, mediator release, and articular metabolism in acute inflammation of innervated or denervated isolated equine joints. Am J Vet Res; 59(1): 88-100.

Huakinsson E C, Berry H, Gishen P. (1995) Effects of anti-inflammatory drugs on the progression of osteoarthritis of the knee. J Rheumatol, 22:1941-1946.

Hungin A P, Kean W F. (2001) Nonsteroidal anti-inflammatory drugs: overused or underused in osteoarthritis? Am J Med; 110(1A):8S-11S.

Iimoto S, Watanabe S, Takahashi T, Shimizu A, Yamamoto H. (2005) The influence of Celecoxib on matrix synthesis by chondrocytes under mechanical stress in vitro. Int J Mol Med; 16(6):1083-8.

Jacobsen S, Niewold T A, Halling-Thomsen M, Nanni S, Olsen E, Lindegaard C, Andersen P H. (2006) Serum amyloid A isoforms in serum and synovial fluid in horses with lipopolysaccharide-induced arthritis. Vet Immunol Immunopathol; 110(3-4):325-30

Karatay S, Kiziltunc A, Yildirim K, Karanfil R C, Senel K. (2005) Effects of different hyaluronic acid products on synovial fluid NO levels in knee osteoarthritis. Clin Rheumatol; 24(5):497-501.

Kato H, Ohashi T, Nakamura N, Nishimura Y, Watari T, Goitsuka R, Tsujimoto H, Hasegawa A. (1995) Molecular cloning of equine interleukin-1 alpha and -beta cDNAs. Vet Immunol Immunopathol; 48(3-4):221-231.

Kumar D A, Raju K V, Settu K, Kumanan K, Puvanakrishnan R. (2005) Effect of a derivatized tetrapeptide from lactoferrin on nitric oxide mediated matrix metalloproteinase-2 production by synovial fibroblasts in collagen-induced arthritis in rats. Peptides; 27(6):1434-42.

Kydd A S, Reno C R, Tsao H W, Hart D A. (2007) Early inflammatory arthritis in the rabbit: the influence of intraarticular and systemic corticosteroids on mRNA levels in connective tissues of the knee. J Rheumatol; 34(1):130-9.

Marciani L, Bush D, Wright P, Wickham M, Pick B, Wright J, Faulks R, Fillery-Travis A, Spiller R C, Gowland P A. (2005) Monitoring of gallbladder and gastric coordination by EPI. J Magn Reson Imaging; 21(1):82-85.

Mesa Garcia M D, Aguilera Garcia C M, Gil Hernandez A. (2006) Importance of lipids in the nutritional treatment of inflammatory diseases. Nutr Hasp; 21 Suppl 2:28-41, 30-43.

Nishimoto S, Takagi M, Wakitani S, Nihira T, Yoshida T. (2005) Effect of chondroitin sulfate and hyaluronic acid on gene expression in a three-dimensional culture of chondrocytes. J Biosci Bioeng; 100(1):123-6.

Pavlovic S, Du B, Sakamoto K, Khan K M, Natarajan C, Breyer R M, Dannenberg A J, Falcone D J. (2006) Targeting prostaglandin E2 receptors as an alternative strategy to block cyclooxygenase-2-dependent extracellular matrix-induced matrix metalloproteinase-9 expression by macrophages. J Biol Chem; 281(6):3321-8.

Pearson W, Orth M W, Karrow N A, MacLusky N, Lindinger M I (2007) Anti-inflammatory and chondroprotective effects of nutraceuticals in a cartilage explant model of inflammation. Mol Nutr Food Res: (2007, 51, 1020-1030.

Petrov R, MacDonald M H, Tesch A M, Benton H P. (2005) Inhibition of adenosine kinase attenuates interleukin-1- and lipopolysaccharide-induced alterations in articular cartilage metabolism. Osteoarthritis Cartilage; 13(3):250-7.

Pivnenko T N, Sukhoverkhova Glu, Epshtein L M, Somova-Isachkova L M, Timchenko N F, Besednova N N. (2005) [Experimental morphological study of the therapeutic effect of shark cartilage preparation in a model of infective allergic arthritis] Antibiot Khimioter; 50(5-6):20-3.

Pollard B, Guilford W G, Ankenbauer-Perkins K L, Hedderley D. (2006) Clinical efficacy and tolerance of an extract of green-lipped mussel (*Perna canaliculus*) in dogs presumptively diagnosed with degenerative joint disease. N Z Vet J; 54(3):114-8.

Rashad S, Revell P, Hemingway A, Low F, Rainsford K, Walker F. (1989) Effect of non-steroidal anti-inflammatory drugs on the course of osteoarthritis. Lancet, 2(8662):519-22.

Rininger J A, Kickner S, Chigurupati P, McLean A, Franck Z. (2000) Immunopharmacological activity of Echinacea preparations following simulated digestion on murine macrophages and human peripheral blood mononuclear cells. J Leukoc Biol; 68(4):503-10.

Schena M, Shalon D, Davis R W, Brown P O. Quantitative monitoring of gene expression patterns with a complementary DNA microarray. *Science;* 270:467-470.

Simmons E J, Bertone A L, Weisbrode S E. (1999) Instability-induced osteoarthritis in the metacarpophalangeal joint of horses. Am J Vet Res; 60(1):7-13.

Soder S, Roach H I, Oehler S, Bau B, Haag J, Aigner T. (2006) MMP-9/gelatinase B is a gene product of human adult articular chondrocytes and increased in osteoarthritic cartilage. Clin Exp Rheumatol; 24(3):302-4.

Steel C M, Hopper B J, Richardson J L, Alexander G R, Robertson I D. (2006) Clinical findings, diagnosis, prevalence and predisposing factors for lameness localised to the middle carpal joint in young Standardbred racehorses. Equine Vet J; 38(2):152-7.

Su X Q, Antonas K N, Li D. (2004) Comparison of n-3 polyunsaturated fatty acid contents of wild and cultured Australian abalone. Int J Food Sci Nutr; 55(2):149-54.

Toutain P L, Cester C C. (2004) Pharmacokinetic-pharmacodynamic relationships and dose response to meloxicam in horses with induced arthritis in the right carpal joint. Am J Vet Res; 65(11):1533-41.

van den Boom R, van de Lest C H, Bull S, Brama R A, van Weeren P R, Barneveld A. (2005) Influence of repeated arthrocentesis and exercise on synovial fluid concentrations of nitric oxide, prostaglandin E2 and glycosaminoglycans in healthy equine joints. Equine Vet J; 37(3): 250-6.

Welch R D, Watkins J P, DeBowes R M, Leipold H W. (1991) Effects of intra-articular administration of dimethylsulfoxide on chemically induced synovitis in immature horses. Am J Vet Res; 52(6):934-9.

Yammani R R, Carlson C S, Bresnick A R, Loeser R F. (2006) Increase in production of matrix metalloproteinase 13 by human articular chondrocytes due to stimulation with S100A4: Role of the receptor for advanced glycation end products. Arthritis Rheum; 54(9):2901-11.

Yang I V, Chen E, Hasseman J R Liang W, Frank B C, Wang S, Sharov V, Saeed A I, White J, Li J, Lee N H, Yeatman T J, Quackenbush J. (2002) Within the fold: assessing differential expression measures and reproducibility in microarray assays. Genome Biol; 3(11):0062.

Yashura R, Miyamoto Y, Akaike T, Akuta T, Nakamura M, Takami M, Morimura N, Yasu K, Kamijo R. (2005) Interleukin-1β induces death in chondrocyte-like ATDC5 cells through mitochondrial dysfunction and energy depletion in a reactive nitrogen and oxygen species-dependent manner. Biochem J; 389:315-323.

The invention claimed is:

1. A method of treatment for cartilage degradation in a mammal, the method including administering to the mammal a composition which includes a therapeutic amount of an extract from a seed of a *Biota orientalis* plant, wherein the method includes stimulating cartilage growth or repair through stimulation of at least one eicosanoid prostanoid receptor involved in chondrocyte proliferation which comprises administering to said mammal said extract of said seed of said *Biota orientalis* plant in an effective amount to stimulate said chondrocyte proliferation.

2. The method of claim 1, wherein the composition includes an additional extract selected from the group consisting of perna mussel extract, abalone extract or powder or combinations thereof.

3. The method of claim 1, wherein the composition includes shark cartilage powder.

* * * * *